United States Patent
Fukuoka et al.

(10) Patent No.: US 6,849,738 B2
(45) Date of Patent: Feb. 1, 2005

(54) PROCESSES FOR THE PRODUCTION OF THIENOPYRIMIDINE DERIVATIVES

(75) Inventors: Koichiro Fukuoka, Osaka (JP); Hiroaki Yamamoto, Kawanishi (JP); Kazuhiro Kimura, Suita (JP); Junichi Kawakami, Ikoma (JP); Shokyo Miki, Toyonaka (JP)

(73) Assignee: Takeda Chemical Industries, Ltd., Osaka (JP)

( * ) Notice: Subject to any disclaimer, the term of this patent is extended or adjusted under 35 U.S.C. 154(b) by 336 days.

(21) Appl. No.: 10/220,233

(22) PCT Filed: Feb. 27, 2001

(86) PCT No.: PCT/JP01/01447

§ 371 (c)(1),
(2), (4) Date: Aug. 27, 2002

(87) PCT Pub. No.: WO01/64683

PCT Pub. Date: Sep. 9, 2001

(65) Prior Publication Data

US 2003/0055269 A1 Mar. 20, 2003

(30) Foreign Application Priority Data

Feb. 29, 2000 (JP) .................................... 2000-105769

(51) Int. Cl.$^7$ .................... C07D 495/04; C07D 333/38
(52) U.S. Cl. ............................ 544/278; 549/68
(58) Field of Search ............................ 544/278; 549/68

(56) References Cited

U.S. PATENT DOCUMENTS

| | | | |
|---|---|---|---|
| 4,240,820 A | 12/1980 | Dickoré et al. ................. | 71/76 |
| 4,701,528 A | 10/1987 | Thompson et al. ............. | 544/250 |
| 6,159,962 A | 12/2000 | Steiner et al. ................. | 514/211.08 |
| 6,297,379 B1 | 10/2001 | Furuya et al. ................ | 544/278 |
| 6,340,686 B1 | 1/2002 | Furuya et al. ................ | 514/258 |

FOREIGN PATENT DOCUMENTS

| | | |
|---|---|---|
| JP | 9-6-169766 | 9/1997 |
| WO | WO 95/28405 | 10/1995 |
| WO | WO 96/24597 | 8/1996 |
| WO | WO 97/14697 | 4/1997 |

OTHER PUBLICATIONS

Langhals, H. et al, Chemische Berichte 114(12) pp. 3813–3830, 1981.*
Walker, et al. "Synthesis of Methyl Ketones from Diethyl Acylmalonates" J. Am. Chem. Soc. 68: 1386–1388 (1946).

* cited by examiner

Primary Examiner—Thomas C. McKenzie
(74) Attorney, Agent, or Firm—Mark Chao; Elaine M. Ramesh

(57) ABSTRACT

The present invention provides a process for producing an intermediate for thienopyrimidine derivatives having the GnRH antagonistic activity at an industrial large scale.

The process for production of the present invention relates to a process for producing a compound represented by the formula (III):

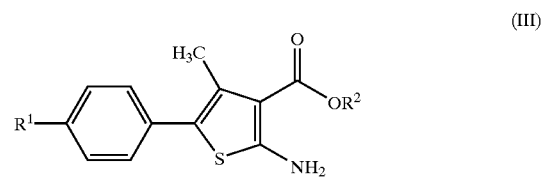

(III)

wherein respective symbols have the same meanings as those described below, or a salt thereof, which comprises subjecting a compound represented by the formula (I):

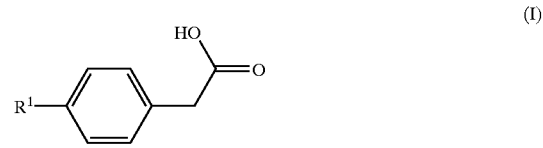

(I)

wherein $R^1$ denotes hydrogen, nitro, halogen, phthalimido, mono- or di-(alkylcarbonyl)amino or alkoxy, or a salt thereof, to an acid halogenating reaction, which is successively reacted with malonic acid ester and magnesium alkoxide, treated with an acid, and reacted with sulfur and a compound represented by the formula: $NCCH_2COOR^2$ [wherein $R^2$ denotes alkyl or aryl], or a salt thereof, in the presence of primary amine. According to the process of production of the present invention, thienopyrimidine derivatives having the GnRH antagonistic activity can be produced effectively and at an industrial large scale by a high yield and simple method.

10 Claims, No Drawings

PROCESSES FOR THE PRODUCTION OF THIENOPYRIMIDINE DERIVATIVES

This application is the National Phase filing of International Patent Application No. PCT/JIP01/01447, filed Feb. 27, 2001.

FIELD OF THE INVENTION

The present invention relates to a process for producing thienopyrimidine derivatives which are useful as a medicine and show the useful Gonadotropin releasing hormone [GnRH] antagonistic activity, and intermediates therefor.

BACKGROUND ART

As a process for producing a thieno[2,3-d]pyrimidine compound showing the GnRH antagonistic activity, there is a known method for obtaining a thieno[2,3-d]pyrimidine compound by using, as a starting material, 2-amino-4-methyl-5-(4-nitrophenyl)thiophene-3-carboxylic acid ethyl ester which is obtained by reacting 4-nitrophenylacetone with ethyl cyanoacetate, ammonium acetate, acetic acid, sulfur and diethylamine [WO96/24597(JP-A 9-169768)].

In addition, as a process for producing 2-amino-3-ethoxycarbonyl-4-methyl-5-phenylthiophene, there is a known method of acting morphorine or triethylamine on a solution of phenylacetone, ethyl cyanoacetate and sulfur in ethanol (U.S. Pat. No. 4,240,820 etc.).

On the other hand, as a process for producing a methylketone compound, there is a known method of subjecting a magnesium ethoxy derivative of diethyl malonate and a suitable amount of acid chloride to an acylating reaction, which is subjected to a hydrolysis reaction, and subjecting (two ester groups of) the resulting diethyl acylmalonate to a decarboxylation reaction in the presence of an acid (J.Am.Chem.Soc., Vol.68,pp1386(1946)etc.).

In the previous process of production, there are problems that the expensive starting materials are used, high toxic carbon tetrachloride is used, high risky metal magnesium is used, and a compound having the strong skin stimulating property is isolated and, therefore, an industrially advantageous process for producing thieno[2,3-d]pyrimidine derivatives showing the GnRH antagonistic activity is desired.

SUMMARY OF THE INVENTION

The present inventors extensively studied a process for producing thieno[2,3-d]pyrimidine derivatives, found that thieno[2,3-d]pyrimidine derivatives of interest showing the GnRH antagonistic activity can be unexpectedly obtained safely, simply and at a high yield by using 4-nitrophenylacetone, magnesium alkoxide and primary amine as a starting material for the first time and this process is sufficiently satisfactory at an industrial scale, and completed the present invention based on these findings.

That is, the present invention relates to:
[1] a process for producing a compound represented by the formula(III):

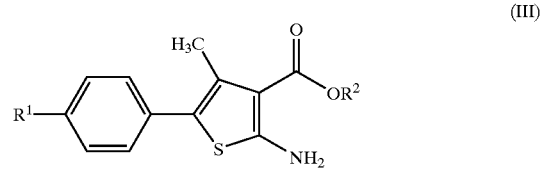

wherein respective symbols have the same meanings as those described below, or a salt thereof, which comprises:
subjecting a compound represented by the formula (I):

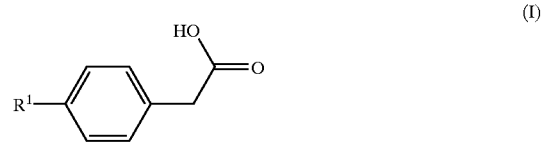

wherein $R^1$ denotes a hydrogen atom, nitro, halogen, phthalimido, mono(alkylcarbonyl)amino, di(alkylcarbonyl)amino or alkoxy, or a salt thereof, to an acid halogenating reaction, which is successively reacted with malonic acid ester and magnesium alkoxide and, thereafter, treated with an acid and, then, reacted with sulfur and a compound represented by the formula (II):

wherein $R^2$ denotes alkyl or aryl, or a salt thereof, in the presence of primary amine,
[2] the process described in the [1], wherein $R^1$ is nitro;
[3] the process described in the [1], wherein the primary amine is mono-$C_{3-8}$ alkylamine:
[4] a process for producing a compound represented by the formula(XII):

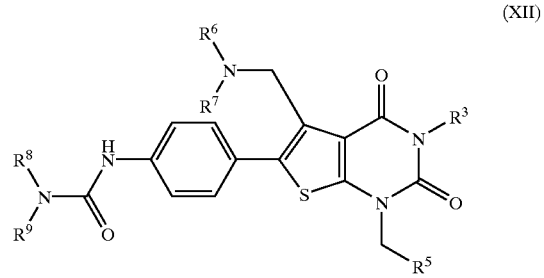

wherein respective symbols have the same meanings as those described below, which comprises:
subjecting a compound represented by the formula($I^a$):

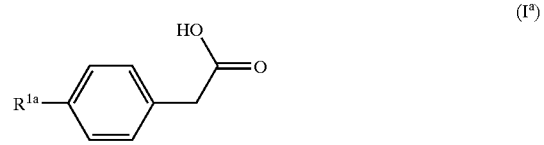

wherein $R^{1a}$ denotes nitro, phthalimido, mono(alkylcarbonyl)amino or di(alkylcarbonyl)amino, or a salt thereof, to an acid halogenating reaction, which is successively reacted with malonic acid ester and magnesium alkoxide and, thereafter, treated with an acid and, then, reacted with a sulfur and a compound represented by the formula(II):

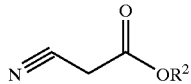
(II)

wherein $R^2$ denotes alkyl or aryl, or a salt thereof in the presence of primary amine, to obtain a compound represented by the formula (III):

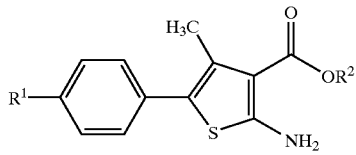
(III)

wherein respective symbols have the same meanings as those described above, or a salt thereof and, then, reacting the compound (III) or a salt thereof with a compound represented by the formula(IV):

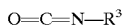
(IV)

wherein $R^3$ denotes alkyl optionally having a substituent or aryl optionally having a substituent, or a salt thereof, to obtain a compound represented by the formula (V):

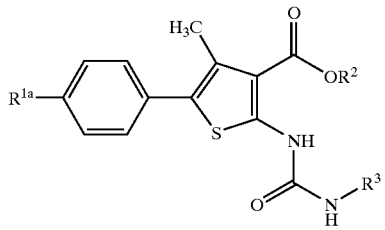
(V)

wherein respective symbols have the same meanings as those described above, or a salt thereof and, then, subjecting the compound (V) or a salt thereof to a ring closing reaction, which is reacted with a compound represented by the formula(VI):

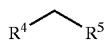
(VI)

wherein $R^4$ denotes a leaving group, and $R^5$ denotes aryl optionally having a substituent, or a salt thereof, to obtain a compound represented by the formula (VII):

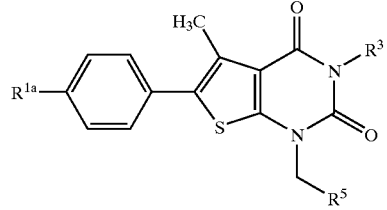
(VII)

wherein respective symbols have the same meanings as those described above, or a salt thereof and, then, subjecting the compound (VII) or a salt thereof to a brominating reaction, which is successively reacted with a compound represented by the formula (VIII):

(VIII)

wherein $R^6$ and $R^7$ denote alkyl optionally having a substituent, aryl optionally having a substituent, alkoxy optionally having a substituent, aralkyl optionally having a substituent or a heterocycle group optionally having a substituent, or a salt thereof, to obtain a compound represented by the formula (IX):

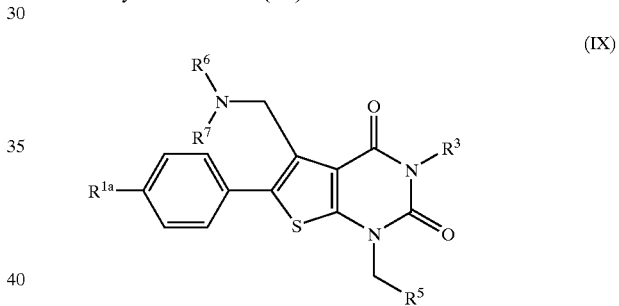
(IX)

wherein respective symbols have the same meanings as those described above, or a salt thereof, and (1) when $R^{1a}$ is nitro, subjecting the compound (IX) or a salt thereof to a reducing reaction,
(2) when $R^{1a}$ is phthalimido, subjecting the compound (IX) or a salt thereof to a deprotecting reaction, or
(3) when $R^{1a}$ is mono(alkylcarbonyl)amino or di(alkylcarbonyl)amino, subjecting the compound (IX) or a salt thereof to a hydrolyzing reaction, to obtain a compound represented by the formula (X):

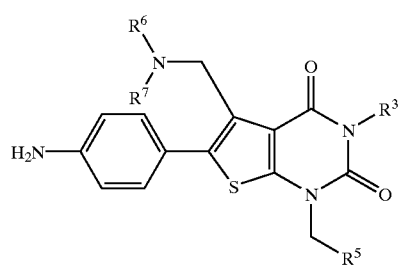
(X)

wherein respective symbols have the same meanings as those described above, or a salt thereof and, then, (i) reacting the compound (X) or a salt thereof, with halogenoformic acid ester and a compound represented by the formula (XI):

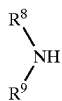

(XI)

wherein $R^8$ and $R^9$ denote a hydrogen atom, alkoxy optionally having a substituent or alkyl optionally having a substituent, or a salt thereof, or (ii) reacting the compound (X) or a salt thereof with carbonyldiimidazole and a compound represented by the formula (XI):

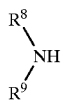

(XI)

wherein respective symbols have the same meanings as those described above or a salt thereof;

[5] the process described in the [4], wherein $R^{1a}$ is nitro;

[6] the process described in the [4], wherein $R^3$ is phenyl optionally having a substituent;

[7] the process described in the [4], wherein $R^5$ is phenyl optionally having a substituent;

[8] the process described in the [4], wherein one of $R^6$ and $R^7$ is $C_{1-3}$ alkyl, and the other of them is benzyl optionally having a substituent;

[9] the process described in the [4], wherein one of $R^8$ and $R^9$ is a hydrogen atom, and the other of them is $C_{1-3}$ alkoxy;

[10] the process described in the [4], wherein the compound (VII) or a salt thereof is subjected to a brominating reaction in the presence of bromine and a radical initiator.

BEST MODE FOR CARRYING OUT THE INVENTION

In the aforementioned formulas, examples of the "halogen" denoted by $R^1$ include fluoro, chloro, bromo and iodo.

Examples of the "mono(alkylcarbonyl)amino" denoted by $R^1$ or $R^{1a}$ include mono($C_{1-6}$ alkylcarbonyl)amino (for example, acetylamino, propionylamino and the like).

Examples of the "di(alkylcarbonyl)amino" denoted by $R^1$ or $R^{1a}$ include di($C_{1-6}$ alkylcarbonyl)amino (for example, diacetylamino, dipropionylamino and the like).

Examples of the "alkoxy" denoted by $R^1$ include $C_{1-6}$ alkoxy (for example, methoxy, ethoxy, propoxy, butoxy, isopropoxy, isobutoxy, t-butoxy and the like).

As $R^1$ or $R^{1a}$, nitro and phthalimido are preferable. Furthermore nitro is more preferable.

Examples of the "alkyl" denoted by $R^2$ include $C_{1-6}$ alkyl (for example, methyl, ethyl, propyl, isopropyl, butyl, isobutyl, t-butyl, pentyl, hexyl and the like).

Examples of the "aryl" denoted by $R^2$ include $C_{6-14}$ aryl, preferably $C_{6-10}$ aryl (for example, phenyl, 1-naphthyl, 2-naphthyl and the like.

As $R^2$, $C_{1-3}$ alkyl is preferable, and ethyl is more preferable.

Examples of the "alkyl" in the "alkyl optionally having a substituent" denoted by $R^3$ include $C_{1-6}$ alkyl (for example, methyl, ethyl, propyl, isopropyl, butyl, isobutyl, t-butyl, pentyl, hexyl and the like).

Examples of the "substituent" in the "alkyl optionally having a substituent" denoted by $R^3$ include (i) $C_{1-6}$ alkoxy (for example, methoxy, ethoxy, propoxy, butoxy, isopropoxy, isobutoxy, t-butoxy and the like) (ii) $C_{1-4}$ acyl (for example, $C_{1-3}$ alkyl-carbonyl such as acetyl and propionyl and the like) and (iii) $C_{6-14}$ aryl optionally having a substituent. The number of the substituent is 1 to 5 at replaceable positions. Examples of the "$C_{6-14}$ aryl optionally having a substituent" include the same "aryl optionally having a substituent" as that denoted by $R^3$ described later.

Examples of the "aryl" in the "aryl optionally having a substituent" denoted by $R^3$ include $C_{6-14}$ aryl, preferably $C_{6-10}$ aryl (for example, phenyl, 1-naphthyl, 2-naphthyl and the like), particularly preferably phenyl.

Examples of the "substituent" in the "aryl optionally having a substituent" denoted by $R^3$ include (i) halogen (for example, fluorine, chlorine, bromine, iodine), (ii) $C_{1-6}$ alkyl (for example, methyl, ethyl, propyl, isopropyl, butyl, isobutyl, t-butyl, pentyl, hexyl and the like), (iii) $C_{1-6}$ alkoxy (for example, methoxy, ethoxy, propoxy, butoxy, isopropoxy, isobutoxy, t-butoxy and the like) optionally having 1 to 3 substituents selected from halogen (for example, fluorine, chlorine, bromine, iodine), hydroxy and $C_{1-3}$ alkyl (for example, methyl, ethyl, propyl, isopropyl and the like), and (iv) $C_{1-4}$ acyl (for example, $C_{1-3}$ alkyl-carbonyl such as acetyl and propionyl and the like). The number of the substituent is 1 to 3 at replaceable positions.

As $R^3$, phenyl optionally having a substituent is preferable, and unsubstituted phenyl is more preferable.

Examples of the "leaving group" denoted by $R^4$ include halogen (for example, fluorine, chlorine, bromine, iodine), alkylsulfonyloxy (for example, $C_{1-6}$ alkylsulfonyloxy such as methylsulfonyloxy and the like), arylsulfonyloxy (for example, $C_{6-14}$ arylsulfonyloxy (for example, phenylsulfonyloxy and the like) optionally substituted with 1 to 5 of $C_{1-6}$ alkyl (for example, methyl, ethyl, propyl, isopropyl, butyl, isobutyl, t-butyl, pentyl, hexyl and the like) such as p-toluenesulfonyloxy and the like).

Examples of the "aryl optionally having a substituent" denoted by $R^5$ include the same "aryl optionally having a substituent" as that denoted by $R^3$.

As $R^5$, phenyl optionally having a substituent is preferable. Phenyl optionally having 1 or 2 halogen atoms (for example, fluorine, chlorine, bromine and iodine) is more preferable, and 2,6-difluorophenyl is the most preferable.

Examples of the "alkyl optionally having a substituent" denoted by $R^6$ or $R^7$, include the same "alkyl optionally having a substituent" as that denoted by $R^3$.

Examples of the "aryl optionally having a substituent" denoted by $R^6$ or $R^7$ include the same "aryl optionally having a substituent" as that denoted by $R^3$.

Examples of the "alkoxy" in the "alkoxy optionally having a substituent" denoted by $R^6$ or $R^7$ include $C_{1-6}$ alkoxy (for example, methoxy, ethoxy, propoxy, isopropoxy, butoxy, isobutoxy, t-butoxy and the like) and the like.

Examples of the "substituent" in the "alkoxy optionally having a substituent" denoted by $R^6$ or $R^7$ include carboxy, $C_{1-3}$ alkyl (for example, methyl, ethyl, propyl, isopropyl and the like) and $C_{1-4}$ acyl ($C_{1-3}$ alkyl-carbonyl such as acetyl and propionyl). The number of the substituent is 1 to 3 at replaceable positions.

Examples of the "aralkyl" in the "aralkyl optionally having a substituent" denoted by $R^6$ or $R^7$ include $C_{7-16}$ aralkyl (for example, benzyl, phenethyl, 1-naphthylmethyl, 2-naphthylmethyl and the like), preferably benzyl and the like.

Examples of the "heterocycle group" in the "heterocycle group optionally having a substituent" denoted by $R^6$ or $R^7$ include 5 to 6-membered heterocycle groups containing 1 to 3 hetero atoms selected from a nitrogen atom, a sulfur atom and an oxygen atom in addition to a carbon atom, more specifically, thienyl (for example, 2-thienyl, 3-thienyl and the like), pyridyl (for example, 2-pyridyl, 3-pyridyl, 4-pyridyl and the like), furyl (for example, 2-furyl, 3-furyl and the like), pyrazinyl, pyrimidinyl( for example, 2-pyrimidinyl and the like), pyrolyl (for example, 3-pyrolyl and the like), pyridazinyl (for example, 3-pyridazinyl and the like), isothiazolyl (for example, 3-isothiazolyl and the like), isoxazolyl (for example, 3-isoxazolyl and the like), pyrrolidinyl (for example, 1-pyrrolidinyl, 2-pyrrolidinyl, 3-pyrrolidinyl and the like), imidazolinyl (for example, 2-imidazolinyl, 4-imidazolinyl and the like), pyrazolidinyl (for example, 2-pyrazolidinyl, 3-pyrazolidinyl, 4-pyrazolidinyl and the like), piperidino, piperidyl (for example, 2-piperidyl, 3-peperidyl, 4-peperidyl), piperazinyl (for example, 1-piperazinyl, 2-piperazinyl and the like), morpholinyl (for example, morpholino and the like).

Examples of the "substituent" in the "aralkyl optionally having a substituent" and the "heterocycle group optionally having a substituent" denoted by $R^6$ or $R^7$ include $C_{1-6}$ alkyl (for example, methyl, ethyl and the like), $C_{1-6}$ alkoxy (for example, methoxy, ethoxy and the like), $C_{1-6}$ alkylthio (for example, methylthio, ethylthio and the like), $C_{1-4}$ acyl (for example, $C_{1-3}$ alkyl-carbonyl such as acetyl and propionyl and the like) and di-$C_{1-6}$ alkylamino (for example, dimethyl amino and the like). The number of substituent is 1 to 5 at replaceable positions.

As $R^6$ or $R^7$, it is preferable that one of them is $C_{1-3}$ alkyl and the other is benzyl optionally having a substituent, and it is more preferable that one of them is $C_{1-3}$ alkyl and the other is benzyl.

Examples of the "alkoxy" in the "alkoxy optionally having a substituent" denoted by $R^8$ or $R^9$ include $C_{1-6}$ alkoxy (for example, methoxy, ethoxy, propoxy, isopropoxy, butoxy, isobutoxy, t-butoxy and the like).

Examples of the "alkyl" in the "alkyl optionally having a substituent" denoted by $R^8$ or $R^9$ include $C_{1-6}$ alkyl (for example, methyl, ethyl, propyl, isopropyl, butyl, isobutyl, t-butyl, pentyl, hexyl and the like).

Examples of the "substituent" in the "alkoxy optionally having a substituent" and the "alkyl optionally having a substituent" denoted by $R^8$ or $R^9$ include (i) hydroxy, (ii) $C_{1-7}$ acyloxy (for example, $C_{1-6}$ alkyl-carbonyloxy such as acetoxy and propionyloxy), (iii) benzoyloxy, (iv) amino optionally having 1 or 2 substituents selected from $C_{1-6}$ alkoxy-carbonyl (for example, methoxycarbonyl, ethoxycarbonyl, tert-butoxycarbonyl and the like), benzyloxycarbonyl, $C_{1-4}$ acyl ($C_{1-3}$ alkyl-carbonyl such as acetyl and propionyl and the like), $C_{1-4}$ alkyl (for example, methyl, ethyl, propyl, butyl and the like) and $C_{1-3}$ alkylsulfonyl (for example, methanesulfonyl and the like) and the like (for example, amino, dimethylamino, methoxycarbonylamino, ethoxycarbonylamino, t-butoxycarbonylamino, benzyloxycarbonylamino, acetylamino, methanesulfonylamino and the like), (v) $C_{1-10}$ alkoxy (for example, methoxy, ethoxy, propoxy, t-butoxy and the like), (vi) $C_{3-7}$ cycloalkyloxycarbonyloxy-$C_{1-3}$ alkoxy (for example, 1-(cyclohexyloxycarbonyloxy)ethoxy and the like), and (vii) $C_{1-3}$ alkoxy-$C_{1-3}$ alkoxy (for example, methoxymethoxy, methoxyethoxy and the like). The number of the substituent is 1 to 5 at replaceable positions.

As $R^8$ and $R^9$, it is preferable that one of them is a hydrogen atom and the other is $C_{1-3}$ alkoxy.

As salts of compounds represented by the formulas (I)–(XIII) and (I$^a$) herein, pharmaceutically acceptable salts are preferable, and examples thereof include salts with an inorganic acid, salts with an organic acid, salts with an inorganic base and salts with an organic base.

Examples of the salt with an inorganic acid include salts with hydrochloric acid, hydrobromic acid, nitric acid, sulfuric acid and phosphoric acid and the like.

Examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid and the like.

Examples of the salt with an inorganic base include alkali metal salts such as sodium salt and potassium salt; alkaline earth metal salts such as calcium salt and magnesium salt; ammonium salt and the like.

Examples of the salt with an organic base include salts with trimethylamine, triethylamine, pyridine, picoline, ethanolamine, diethanolamine, triethanolamine, dicyclohexylamine and N,N'-dibenzylethylenediamine and the like.

Hereinafter, a compound represented by the formula (I) or salt thereof is abbreviated as "Compound (I)". Other compounds are abbreviated in a similar manner. A process for producing Compound (III) which is useful as an intermediate for thienopyrimidine derivatives showing the GnRH antagonistic activity is described below.

When Compound (I), Compound (I$^a$), Compound (II), Compound (IV), Compound (VI), Compound (VIII) and Compound (XI) are commercially available, sold products may be used as they are, or these compounds may be prepared according to the method known per se or a similar method thereof.

(Step 1A)

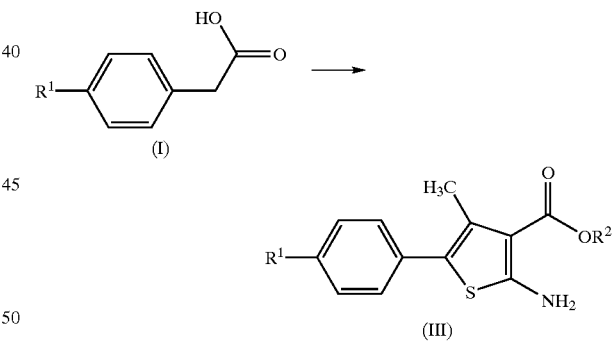

wherein $R^1$ denotes a hydrogen atom, nitro, halogen, phthalimido, mono(alkylcarbonyl)amino, di(alkylcarbonyl) amino or alkoxy, and $R^2$ denotes the same meanings as those described above.

Compound (I) is subjected to an acid halogenating reaction, which is successively reacted with malonic acid ester and magnesium alkoxide and, then, treated with an acid and, then, reacted with sulfur and Compound (II) in the presence of primary amine to obtain Compound (III).

① Acid Halogenating Reaction

An acid halogenating reaction for Compound (I) may be performed according to the method known per se, for example, by reacting Compound (I) and an acid halogenating agent (for example, thionyl chloride, thionyl bromide, oxalyl chloride and the like).

The amount of the acid halogenating agent to be used is about 1–4 moles, preferably about 1.5–3 moles relative to 1 mole of Compound (I).

It is advantageous that the present reaction is performed without any solvent or in the presence of a solvent which is inert with the reaction. Examples of the solvent is not particularly limited as far as the reaction proceeds, and include halogenated hydrocarbons, aliphatic hydrocarbons, aromatic hydrocarbons, ethers, esters, amides, nitriles and a mixture of 2 or more of them.

The reaction temperature is usually about 0–100° C., preferably about 0–80° C. The reaction time is usually about 0.5–3 hours, preferably about 0.5–1 hour. The present reaction may be performed optionally in the presence of N,N-dimethylformamide or the like.

The amount of N,N-dimethylformamide to be used is about 0–1 mole, preferably about 0–0.5 mole relative to 1 mole of Compound (I).

The product:

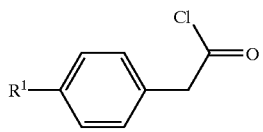

maybe used in the next reaction as the reaction solution itself or as the crude product, or may be isolated from the reaction mixture according to the conventional method and may serve as a starting material in the next step.

② Reaction with Malonic Acid Ester and Magnesium Alkoxide.

Examples of the "malonic acid ester" include a compound represented by the formula "$R^aOOC—CH_2—COOR^b$" (wherein $R^a$ and $R^b$ denote alkyl or aryl, respectively).

Examples of the "alkyl" denoted by $R^a$ or $R^b$ include $C_{1-6}$ alkyl (for example, methyl, ethyl, propyl, isopropyl, butyl, isobutyl, t-butyl, pentyl, hexyl and the like).

Examples of the "aryl" denoted by $R^a$ or $R^b$ include $C_{6-10}$ aryl (for example, phenyl, 1-naphthyl, 2-naphthyl and the like).

As $R^a$ and $R^b$, $C_{1-6}$ alkyl is preferable, and ethyl is more preferable.

The amount of the "malonic acid ester" to be used is about 1–2 moles, preferably 1.1–1.3 moles relative to 1 mole of Compound (I).

As the "magnesium alkoxide", magnesium $C_{1-6}$ alkoxide such as magnesium methoxide and magnesium ethoxide and the like is preferable, and magnesium $C_{1-3}$ alkoxide is more preferable.

An amount of the "magnesium alkoxide" to be used is about 1–2 moles, preferably about 1.1–1.3 moles relative to 1 mole of Compound (I).

The present reaction may be performed optionally in the presence of Lewis acid.

Examples of the "Lewis acid" include anhydrous aluminium chloride, titanium tetrachloride and magnesium chloride and the like.

The amount of the "Lewis acid" to be used is about 1–4 moles, preferably about 1–2 moles relative to 1 mole of Compound (I).

It is advantageous that the present reaction is performed in the presence of a solvent which is inert with the reaction. The solvent is not particularly limited as far as the reaction proceeds. For example, halogenated hydrocarbons, aliphatic hydrocarbons, ethers, amides, alcohols or a mixture of 2 or more of them are used. Among them, ethers such as butyl methyl ether (for example, tert-butyl methyl ether and the like), butyl ethyl ether (for example, tert-butyl ethyl ether and the like) are preferable.

The reaction temperature is usually about 20–100° C., preferably about 40–70° C. The reaction time is usually about 1–12 hours, preferably 4–7 hours.

The product:

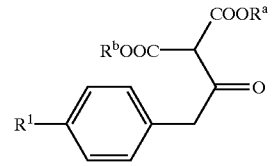

may be used as the reaction solution itself or as the crude product, or may be isolated from the reaction mixture according to the conventional method and may serve as a starting material in the next step.

③ Treatment with an Acid

The hydrolysis reaction is performed by using an acid.

Examples of the "acid" include mineral acids such as hydrochloric acid, hydrobromic acid and sulfuric acid and the like; organic acids such as acetic acid and trifluoroacetic acid and the like, or a mixture of 2 or more of them. Among them, the preferable is a mixture of sulfuric acid and acetic acid.

The amount of the "acid" to be used is about 1–10 moles, preferably 4–8 moles relative to 1 mole of Compound (I).

It is advantageous that the present reaction is performed in the presence of a solvent which is inert with the reaction. The solvent is not particularly limited as far as the reaction proceeds. For example, ethers, amides, alcohols, water or a mixture of 2 or more of them are used. Preferably, water is used.

The reaction temperature is usually about 70–140° C., preferably about 90–130° C. The reaction time is usually about 1–12 hours, preferably about 4–7 hours.

The product:

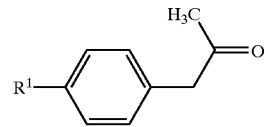

may be used in the next reaction as the reaction solution itself or as the crude product, or may be isolated from the reaction mixture according to the conventional method and may serve as a starting material in the next step.

④ Reaction with Sulfur and Compound (II) in the Presence of Primary Amine

Examples of the "primary amine" include mono-$C_{3-8}$ alkylamine (for example, propylamine, butylamine, octylamine and the like), benzylamine and the like. Among them, butylamine is preferable.

The amount of the "primary amine" to be used is about 0.01–1.5 moles, preferably about 0.1–1.2 moles relative to 1 mole of Compound (I).

As the "sulfur", powdery sulfur and the like is used.

The amount of the "sulfur" to be used is about 1–2 moles, preferably 1–1.2 moles relative to 1 mole of Compound (I).

The amount of the "Compound (II)" to be used is about 1–1.5 moles, preferably about 1–1.2 moles relative to 1 mole of Compound (I).

It is advantageous that the present reaction is performed without any solvent or in the presence of a solvent which is inert with the reaction. The solvent is not particularly limited as far as the reaction proceeds. For example, alcohols, nitriles, ethers, esters, amides, or a mixture of 2 or more of them are used.

Preferably, alcohols such as methanol and ethanol and the like are used.

The reaction temperature is usually about 20–100° C., preferably about 20–70° C. The reaction time is usually 1–12 hours, preferably 1–5 hours.

The product (III) may be used in the next reaction as the reaction solution itself or as the crude product, or may be isolated from the reaction mixture according to the conventional method and may serve as a starting material in the next step.

The aforementioned steps ①–④ may be performed continuously without isolating an intermediate produced in each step from the reaction mixture, and are industrially advantageous.

A Compound wherein $R^1$ is a hydrogen atom, halogen or alkoxy in Compound (III) can be produced according to the following method:
(Step 1B)

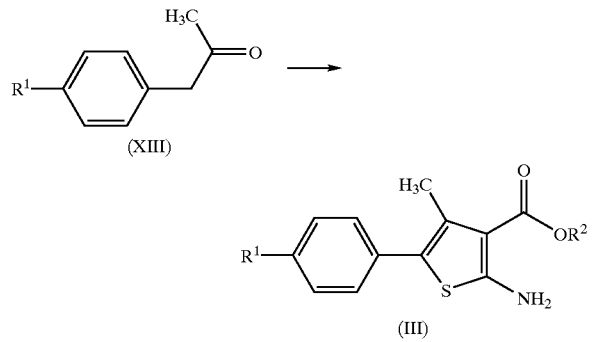

wherein $R^1$ is a hydrogen atom, halogen or alkoxy, and $R^2$ has the same meanings as those described above.

Compound (III) is obtained by reacting Compound (XIII) and Compound (II) in the presence of organic amine, which is then reacted with sulfur and organic amine.

① Reaction with Compound (II)

Examples of the "organic amine" include the aforementioned primary amine and benzyl amine and the like.

The amount of the "Compound (II)" to be used is about 1–1.5 moles, preferably about 1–1.2 moles relative to 1 mole of Compound (XIII).

The amount of the "organic amine" to be used is about 0.005–0.5 mole, preferably about 0.01–0.1 mole relative to 1 mole of Compound (XIII).

It is advantageous that the present reaction is performed without any solvent or in the presence of a solvent which is inert with the reaction. The solvent is not particularly limited as far as the reaction proceeds. For example, alcohols, nitrites, ethers, amides, or a mixture of 2 or more of them and the like are used. Preferably, alcohols are used.

The reaction temperature is usually about 20–80° C., preferably about 20–60° C. The reaction time is usually about 2–10 hours, preferably about 4–8 hours.

The product may be used as the reaction solution itself or as the crude product, or may be isolated from the reaction mixture according to the conventional method and may serve as a starting material in the next step.

② Reaction with Sulfur and Organic Amine

Examples of the "organic amine" include aforementioned primary amine, benzyl amine and morpholine.

The amount of the "sulfur" to be used is about 1–2 moles, preferably about 1–1.2 moles relative to 1 mole of Compound (XIII).

The amount of the "organic amine" to be used is about 0.1–0.7 mole, preferably about 0.3–0.6 mole relative to 1 mole of Compound (XIII).

It is advantageous that the present reaction is performed without any solvent or in the presence of a solvent which is inert with the reaction. The solvent is not particularly limited as far as the reaction proceeds. For example, alcohols, nitriles, ethers, amides, or a mixture of 2 or more of them and the like are used. Preferably, alcohols are used.

The reaction temperature is usually 20–80° C., preferably about 20–60° C. The reaction time is usually about 2–10 hours, preferably about 4–8 hours.

The product (III) may be used in the next reaction as the crude product, or may be isolated from the reaction mixture according to the conventional method and may serve as a starting material in the next step.

The present reaction can suppress the amount of organic amine to be used to a catalytic amount, and is industrially advantageous.

A compound (Compound ($I^a$)) wherein $R^1$ is nitro, phthalimido, mono(alkylcarbonyl)amino or di(alkylcarbonyl)amino in Compound (I), or a salt thereof, may be converted into a thienopyrimidine derivative showing the GnRH antagonistic activity as follows:

(Step 1C)

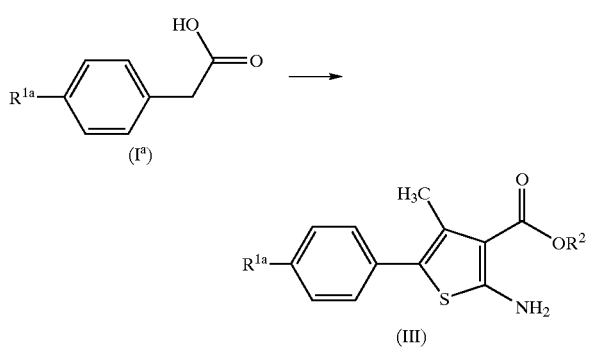

wherein $R^{1a}$ denotes nitro, phthalimido, mono(alkylcarbonyl)amino or di(alkylcarbonyl)amino, and $R^2$ denotes the same meanings as those described above.

Compound ($I^a$) or a salt thereof is subjected to an acid halogenating reaction, which is successively reacted with malonic acid ester and magnesium alkoxide and, thereafter, treated with an acid and, then, reacted with sulfur and Compound (II) in the presence of primary amine to obtain Compound (III).

The present reaction may be performed under the same reaction conditions as those described above (Step 1A).

(Step 2)

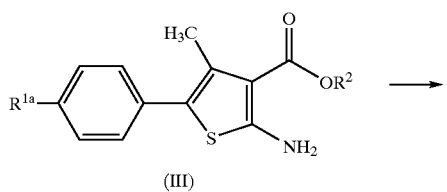

-continued

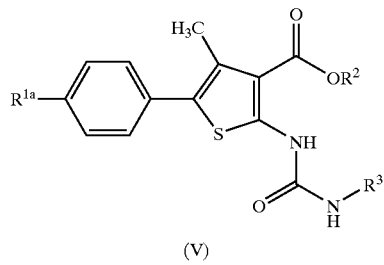

(V)

wherein R$^{1a}$ denotes nitro, phthalimido, mono (alkylcarbonyl)amino or di(alkylcarbonyl)amino, and other symbols denote the same meanings as those described above.

Compound (III) and Compound (IV) are reacted to obtain Compound (V).

The present reaction may advantageously proceed usually in the presence of an organic base and examples of such the "organic base" include amines such as triethylamine, diisopropylethyamine, N-methylmorpholine, dimethylaminopyridine, DBU (1,8-diazabicyclo[5.4.0] undec-7-ene) and DBN (1,5-diazabicyclo[4.3.0]non-5-ene), and basic heterocyclic compounds such as pyridine, imidazole and 2,6-lutidine. Preferably, pyridine is used.

The amount of the "Compound (IV)" to be used is about 1–2 moles, preferably about 1.3–1.7 moles relative to 1 mole of Compound (III).

The amount of the "organic base" to be used is about 1–2.5 moles, preferably about 1.5–2 moles relative to 1 mole of Compound (III).

It is advantageous that the present reaction is performed without any solvent or in the presence of a solvent which is inert with the reaction. The solvent is not particularly limited as far as the reaction proceeds. For example, halogenated hydrocarbons, aliphatic hydrocarbons, aromatic hydrocarbons, ethers, esters, amides, nitrites, alcohols or a mixture of 2 or more of them and the like are used. Preferably, toluene is used.

The reaction temperature is usually about 80–130° C., preferably about 90–110° C. A reaction time is usually about 2–6 hours, preferably about 3–5 hours.

The product (V) may be used in the next reaction as the reaction solution itself or as the crude product, or may be isolated from the reaction mixture according to the conventional method and may serve as a starting material in the next step.

(Step 3)

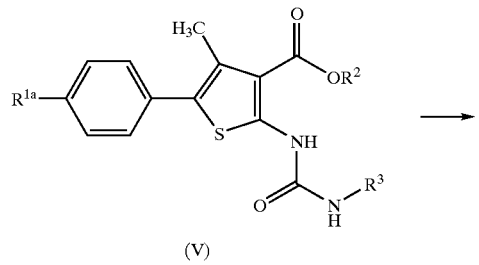

(V)

-continued

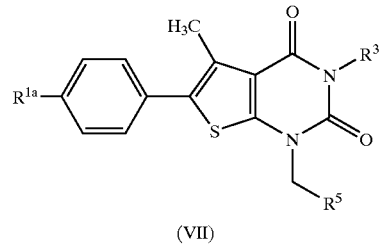

(VII)

wherein R$^{1a}$ denotes nitro, phthalimido, mono (alkylcarbonyl)amino or di(alkylcarbonyl)amino, and other symbols have the same meanings as those described above.

Compound (V) is subjected to a ring closing reaction, which is reacted with Compound (VI) to obtain Compound (VII).

① Ring Closing Reaction

Compound (V) is subjected to a ring closing reaction.

The present reaction may advantageously proceed usually in the presence of a base and examples of such the "base" include strong bases such as hydrides of an alkali metal or an alkaline earth metal (for example, lithium hydride, sodium hydride, potassium hydride, calcium hydride and the like), amides of an alkali metal or an alkaline earth metal (for example, lithium amide, sodium amide, lithium diisopropylamide, lithium dicyclohexylamide, lithium hexamethyldisilazide, sodium hexamethyldisilazide, potassium hexamethyldisilazide and the like) and lower alkoxides of an alkali metal or an alkaline earth metal (for example, sodium methoxide, sodium ethoxide, potassium tert-butoxide and the like). Preferably, lower alkoxides of an alkali metal or an alkaline earth metal are used.

The amount of the "base" to be used is about 1–1.5 moles, preferably about 1.1–1.4 moles relative to 1 mole of Compound (V).

It is advantageous that the present reaction is performed without any solvent or in the presence of a solvent which is inert with the reaction. The solvent is not particularly limited as far as the reaction proceeds. For example, nitriles, alcohols, ethers, amides, halogenated hydrocarbons, aliphatic hydrocarbons, aromatic hydrocarbons, or a mixture of 2 or more of them and the like are used. Preferably, a solvent mixed with an alcohol is used. For example, a mixed solvent of nitrites such as acetonitrile and alcohols such as methanol is preferable.

The reaction temperature is usually about 40–100° C., preferably about 60–90° C. The reaction time is usually about 10 minutes–3 hours, preferably about 30 minutes–2 hours.

The product:

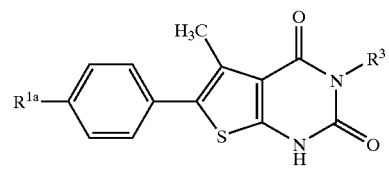

may be used in the next reaction as the reaction solution or as the crude product, or may be isolated from the reaction mixture according to the conventional method and may serve as a starting material in the next step.

② Reaction with Compound (VI)

The amount of the "Compound (VI)" to be used is about 1–2 moles, preferably about 1–1.2 moles relative to 1 mole of Compound (V).

The present reaction may be performed optionally in the presence of a base.

Examples of the "base" include carbonates of an alkali metal or an alkaline earth metal (for example, sodium hydrogen carbonate, sodium carbonate, potassium carbonate and the like), lower alkoxides of an alkali metal or an alkaline earth metal (for example, sodium methoxide, sodium ethoxide, potassium tert-butoxide and the like), organic bases (for example, amines such as triethylamine, diisopropylethylamine, N-methylmorpholine, dimethylaminopyridine, DBU (1,8-diazabicyclo[5.4.0]undec-7-ene) and DBN (1,5-diazabicyclo[4.3.0]non-5-ene), or organic bases such as basic heterocyclic compounds such as pyridine, imidazole and 2,6-lutidine and the like.

The amount of the "base" to be used is about 1–2 moles, preferably about 1–1.3 moles relative to 1 mole of Compound (VII).

It is advantageous that the present reaction is performed without any solvent or in the presence of a solvent which is inert with the reaction. The solvent is not particularly limited as far as the reaction proceeds. For example, nitriles, alcohols, ethers, amides, halogenated hydrocarbons, aliphatic hydrocarbons, aromatic hydrocarbons, or a mixture of 2 or more of them and the like is used. Preferably, a solvent mixed with an alcohol is used. For example, a mixed solvent of nitriles such as acetonitrile and alcohols such as methanol is preferable.

The reaction temperature is usually about 40–100° C., preferably 60–90° C. The reaction time is usually about 1–10 hours, preferably about 3–6 hours.

The product (VII) may be used in the next reaction as the reaction solution itself or as the crude product, or may be isolated from the reaction mixture according to the conventional method and may serve as a starting material in the next step.

The aforementioned steps ①–② may be performed continuously without isolating an intermediate produced in the step ① from the reaction mixture, and are industrially advantageous.

(Step 4)

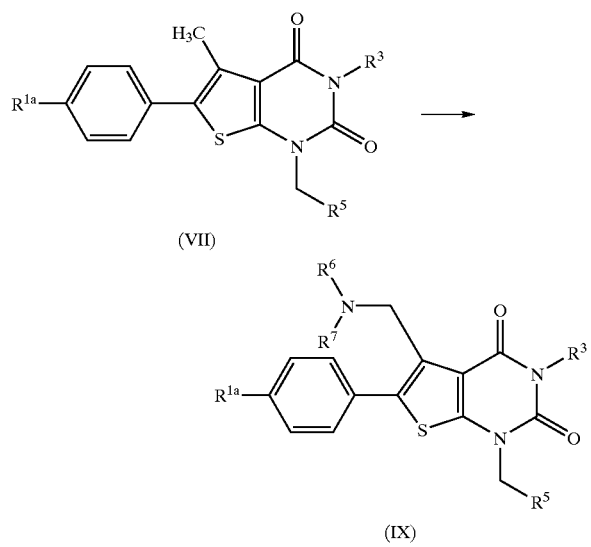

wherein $R^{1a}$ denotes nitro, phthalimido, mono (alkylcarbonyl)amino or di(alkylcarbonyl)amino, and other symbols denote the same meanings as those described above.

Compound (VII) is subjected to a brominating reaction, which is successively reacted with Compound (VIII) to obtain Compound (IX).

① Brominating Reaction

Compound (VII) is reacted with a brominating agent.

Examples of the "brominating agent" include N-bromosuccinimide and 1,3-dibromo-5,5-dimethylhydantoin.

The amount of the "brominating agent" to be used is about 1–3 moles, preferably about 1–1.5 moles relative to 1 mole of Compound (VII).

The present reaction is performed optionally in the presence of bromine and a radical initiator.

The amount of the "bromine" to be used is about 0.01–1 mole, preferably about 0.02–0.3 mole relative to 1 mole of Compound (VII).

Examples of the "radical initiator" include 2,2'-azobis(isobutyronitrile), 2,2'-azobis(2,4-dimethylvaleronitrile) and 2,2'-azobis(4-methoxy-2,4-dimethylvaleronitrile) and the like.

The amount of the "radical initiator" to be used is about 0.01–0.5 mole, preferably about 0.05–0.3 mole relative to 1 mole of Compound (VII).

It is advantageous that the present reaction is performed in the presence of a solvent which is inert with the reaction. The solvent is not particularly limited as far as the reaction proceeds. For example, nitriles, aromatic hydrocarbons, halogenated hydrocarbons, esters, ethers, amides or a mixture of 2 or more of them and the like are used. Preferably, nitriles, aromatic hydrocarbons (chlorobenzene and the like), and halogenated hydrocarbons are used. Among them, nitriles such as acetonitrile are preferable.

The reaction temperature is usually about 20–100° C., preferable 40–90° C. The reaction time is usually about 30 minutes–3 hours, preferably about 1–2 hours.

The product:

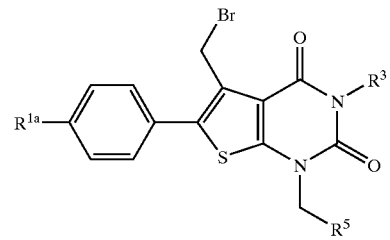

may be used in the next reaction as the reaction solution itself or as the crude product, or may be isolated from the reaction mixture according to the conventional method and may serve as a starting material in the next step.

② Reaction with Compound (VIII)

The amount of the "Compound (VIII)" is about 1–2 moles, preferably about 1–1.3 moles relative to 1 mole of Compound (VII).

The present reaction may advantageously proceed usually under the presence of a base and examples of such the "base" include carbonates of an alkali metal or an alkaline earth metal (for example, sodium hydrogen carbonate, sodium carbonate, potassium carbonate and the like), and organic bases (for example, organic bases such as amines such as triethylamine, diisopropylethylamine, N-methylmorpholine, dimethylaminopyridine, DBU (1,8-diazabicyclo[5.4.0]undec-7-ene), DBN (1,5-diazabicyclo[4.3.0]non-5-ene) and the like, or basic heterocyclic compounds such as pyridine, imidazole, 2,6-lutidine and the like). Preferably, triethylamine and diisopropylethylamine are used.

The amount of the "base" to be used is about 1–2 moles, preferably about 1–1.3 moles relative to 1 mole of Compound (VII).

It is advantageous that the present reaction is performed in the presence of a solvent which is inert with the reaction. The solvent is not particularly limited as far as the reaction proceeds. For example, nitriles, aromatic hydrocarbons, halogenated hydrocarbons, esters, ethers, amides or a mixture of 2 or more of them are used. Preferably, nitriles, aromatic hydrocarbons (chlorobenzene and the like), and halogenated hydrocarbons are used. Among them, nitriles such as acetonitrile are preferable.

The reaction temperature is usually about 0–100° C., preferably about 20–100° C., more preferably about 50–70° C. The reaction time is usually about 10 minutes–2 hours, preferably, about 20 minutes–1.5 hours.

The aforementioned steps ①–② may be continuously performed without isolating an intermediate produced in step ① which is skin stimulating, from the reaction mixture, and are industrially advantageous.
(Step 5)

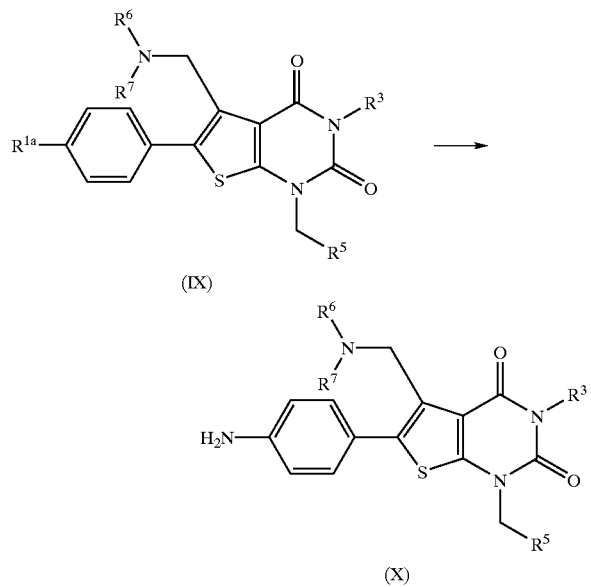

wherein $R^{1a}$ denotes nitro, phthalimido, mono (alkylcarbonyl)amino or di(alkylcarbonyl)amino, and other symbols denote the same meanings as those described above.
(Step 5-1)

When $R^{1a}$ is nitro, Compound (IX) is subjected to a reducing reaction to obtain Compound (X).

In the reducing reaction, Compound (IX) and a reducing agent are reacted.

Examples of the "reducing agent" include a solution of titanium trichloride, iron powder and the like.

Examples of the "solution of titanium trichloride" include an about 10–30% solution of titanium trichloride in water or dilute hydrochloric acid.

The amount of the "reducing agent" to be used is about 1–10 moles, preferably about 3–7 moles relative to 1 mole of Compound (IX).

The present reaction may be performed optionally in the presence of dilute hydrochloric acid.

Examples of the "dilute hydrochloric acid" include an about 0.01–10 mol/l aqueous hydrogen chloride solution.

The amount of the "dilute hydrochloric acid" to be used is about 1–5 moles, preferably about 1–2 moles relative to 1 mole of Compound (IX).

It is advantageous that the present reaction is performed in the presence of a solvent which is inert with the reaction. The solvent is not particularly limited as far as the reaction proceeds. For example, alcohols, esters, ethers, aromatic hydrocarbons, organic acids, water or a mixture of 2 or more of them and the like are used. Preferably, alcohols, organic acids, water or a mixture of 2 or more of them and the like are used.

The reaction temperature is usually about 20–100° C., preferably about 20–80° C. The reaction time is usually about 10 minutes–3 hours, preferably about 20 minutes–2 hours.

The product (X) may be used in the next reaction as the crude product, or may be isolated from the reaction mixture according to the conventional method and may serve as a starting material in the next step.
(Step 5-2)

When $R^{1a}$ is phthalimido, a deprotecting reaction affords Compound (X).

The deprotecting reaction can be performed, for example, by reacting Compound (IX) and hydrazine.

Examples of the "hydrazine" include hydrazine monohydrate and the like.

The amount of the "hydrazine" to be used is about 1–30 moles, preferably about 2–20 moles relative to 1 mole of Compound (IX).

It is advantageous that the present reaction is performed in the presence of a solvent which is inert with the reaction. The solvent is not particularly limited as far as the reaction proceeds. For example, alcohols, ethers, amides, sulfoxides, nitriles, water or a mixture of 2 or more of them and the like are used. Preferably, alcohol, or a mixed solvent with alcohol is used.

The reaction temperature is usually about 20–100° C., preferably about 20–60° C. The reaction time is usually about 1–24 hours, preferably about 2–20 hours.

The product (X) may be used in the next reaction as the crude product, or may be isolated from the reaction mixture according to the conventional method and may serve as a starting material in the next step.
(Step 5-3)

When $R^{1a}$ is mono(alkylcarbonyl)amino or di(alkylcarbonyl)amino, Compound(IX) is subjected to a hydrolyzing reaction to obtain Compound(X).

Compound(IX) is subjected to hydrolysis in the presence of a hydroxide of an alkali metal or an alkaline earth metal, or lower alkoxide of an alkali metal or an alkaline earth metal.

Examples of the "hydroxide of an alkali metal or an alkaline earth metal" include sodium hydroxide, potassium hydroxide, lithium hydroxide and barium hydroxide and the like.

Examples of the "lower alkoxide of an alkali metal or an alkaline earth metal" include sodium methoxide, sodium ethoxide and potassium tert-butoxide.

The amount of the "hydroxide of an alkali metal or an alkaline earth metal" or the "lower alkoxide of an alkali metal or an alkaline earth metal" to be used is about 1–30 moles, preferably about 5–20 moles, respectively, relative to 1 mole of Compound (IX).

It is advantageous that the present reaction is performed in the presence of a solvent which is inert with the reaction. The solvent is not particularly limited as far as the reaction proceeds. For example, alcohols, ethers, sulfoxides, water or a mixture of 2 or more of them and the like are used.

The reaction temperature is usually about 20–140° C., preferably about 60–120° C. The reaction time is usually about 1–24 hours, preferably about 4–18 hours.

The product (X) may be used in the next reaction as the crude product, or may be isolated from the reaction mixture according to the conventional method and may serve as a starting material in the next step.

(Step 6)

[Structure (IX): a thieno-pyrimidinedione core with an aminophenyl substituent, an N-R³ group, an N-R⁵ group, and a CH₂-N(R⁶)(R⁷) substituent, with H₂N- on the phenyl ring]

(IX)

[Structure (XII): similar scaffold as (IX) but the aniline nitrogen is acylated with -NH-C(=O)-CR⁸R⁹ group]

(XII)

wherein respective symbols have the same meanings as those described above.

(Step 6-1)

Compound (X), halogenoformic acid ester (halogenocarbonic acid ester) and Compound (XI) are reacted to obtain Compound (XII).

Examples of the "halogenoformic acid ester" include $C_{6-14}$ aryl halogenocarbonate (for example, phenyl chlorocarbonate, p-nitrophenyl chlorocarbonate and the like) and the like.

The amount of the "halogenoformic acid ester" to be used is about 1–2 moles, preferably about 1–1.3 moles relative to 1 mole of Compound (X).

The amount of the "Compound (XI)" to be used is about 1–10 moles, preferably about 1–6 moles relative to 1 mole of Compound (X).

The present reaction is performed optionally in the presence of an organic base.

Examples of the "base" include organic bases such as amines such as triethylamine, diisopropylethylamine, N-methylmorpholine, dimethylaminopyridine, DBU (1,8-diazabicyclo[5.4.0]undec-7-ene), DBN (1,5-diazabicyclo[4.3.0]non-5-ene) and the like, and basic heterocyclic compounds such as pyridine, imidazole, 2,6-lutidine and the like. Preferably, pyridine and triethylamine are used.

The amount of the "organic base" to be used is about 1–20 moles, preferably about 3–17 moles relative to 1 mole of Compound (X).

It is advantageous that the present reaction is performed in the presence of a solvent which is inert with the reaction. The solvent is not particularly limited as far as the reaction proceeds. For example, esters, ethers, amides, ketones, sulfoxides, nitrites, or a mixture of 2 or more of them and the like are used. Preferably, amides are used.

The reaction temperature is usually about –10 to 80° C., preferably about –10 to 60° C. The reaction time is usually about 1–24 hours, preferably about 5–20 hours.

The product (XII) thus obtained can be isolated from the reaction mixture according to the conventional method.

Compound (XII) can be isolated and purified by the separating means known per se such as recrystallization, distillation, chromatography and the like.

For example, Compound (XII) can be crystallized by adding water or an aqueous solution of carbonate (for example, potassium carbonate and sodium carbonate) to the reaction solution and stirring for a few hours (preferably, 1 hour–1 day). The crystals can be purified by recrystallization from tetrahydrofuran, acetone, methyl ethyl ketone, alcohols (for example, ethanol) or a mixed organic solvent of them (preferably, a mixed organic solvent of tetrahydrofuran and methyl ethyl ketone).

The crystals obtained by such the recrystallization can be further purified to the high purity by suspending in tetrahydrofuran, acetone, methyl ethyl ketone, alcohols (for example, ethanol), water or a mixed organic solvent of them (for example, a mixed solvent of tetrahydrofuran-ethanol, and a mixed solvent of tetrahydrofuran-water), or recrystallizing from these solvents.

When the aforementioned Compound (XII) is obtained as a free compound, it can be converted into a desired salt by the method known per se or a similar method thereof. Conversely, when the Compound (XII) is obtained as a salt, it can be converted into a free compound or a desired other salt according to the method known per se or a similar method thereof.

Compound (XII) may be a hydrate or a non-hydrate. Examples of the hydrate include hemihydrate, monohydrate, sesquihydrate and dihydrate.

When Compound (XII) is obtained as a mixture of optical isomers, a desired dextrorotatory optically active compound or a desired levorotatory optically active compound can be prepared by the optical resolving means known per se.

Compound (XII) may be labeled with an isotope element (for example, $^3H$, $^{14}C$, $^{35}S$).

(Step 6-2)

Compound (X) is reacted with carbonyldiimidazole (N,N'-carbonyldiimidazole) and Compound(XI) to obtain Compound(XII).

The amount of the "carbonyldiimidazole" is about 1–3 moles, preferably about 1–2 moles relative to 1 mole of Compound (X).

The amount of the "Compound (XI)" to be used is about 1–3 moles, preferably about 1–2 moles relative to 1 mole of Compound (X).

The present reaction may be performed optionally in the presence of an organic base.

Examples of the "organic base" include organic bases such as amines such as triethylamine, diisopropylethylamine, N-methylmorpholine, dimethylaminopyridine, DBU (1,8-diazabicyclo[5.4.0]undec-7-ene), DBN (1,5-diazabicyclo[4.3.0]non-5-ene) and the like, and basic heterocyclic compounds such as pyridine, imidazole, 2,6-lutidine and the like. Preferably, triethylamine is used.

The amount of the "organic base" to be used is about 1–2 moles, preferably about 1–1.5 moles relative to 1 mole of Compound (X).

It is advantageous that the present reaction is performed without any solvent or in the presence of a solvent which is inert with the reaction. The solvent is not particularly limited as far as the reaction proceeds. For example, esters, ethers, amides, ketones, sulfoxides, nitriles or a mixture of 2 or more of them and the like are used. Preferably, amides are used.

The reaction temperature is usually about 0–100° C., preferably about 10–70° C. The reaction time is usually about 1–24 hours, preferably about 2–20 hours.

The product (XII) thus obtained can be isolated and purified from the reaction mixture by the conventional method, for example, by the method described in the aforementioned step 6-1 or a similar method thereof.

A compound wherein $R^1$ is a hydrogen atom, halogen or alkoxy in Compound (I), or a salt thereof, can be converted into Compound (IX) [compound wherein $R^1$ is a hydrogen atom, halogen or alkoxy in the formula(IX)] exhibiting the GnRH antagonistic activity, for example, under the same conditions as those for the aformentioned step 1C, step 2, step 3 and step 4.

Examples of the "alcohols" include methanol, ethanol, propanol, isopropanol, t-butanol, ethylene glycol and the like.

Examples of the "ethers" include diethyl ether, diisopropyl ether, t-butyl methyl ether, diphenyl ether, tetrahydrofuran, dioxane, 1,2-dimethoxyethane and the like.

Examples of the "halogenated hydrocarbons" include dichloromethane, chloroform, 1,2-dichloroethane, carbon tetrachloride and the like.

Examples of the "aliphatic hydrocarbons" include hexane, pentane and cyclohexane and the like.

Examples of the "aromatic hydrocarbons" include benzene, toluene, xylene, chlorobenzene and the like.

Examples of the "aromatic amines" include pyridine, lutidine, quinoline and the like.

Examples of the "esters" include methyl acetate, ethyl acetate, ethyl formate and the like.

Examples of the "amides" include N,N-dimethylformamide, N,N-dimethylacetamide, 1-methyl-2-pyrrolidone, hexamethylphosphoric triamide and the like.

Examples of the "ketones" include acetone and methyl ethyl ketone and the like.

Examples of the "sulfoxides" include dimethyl sulfoxide and the like.

Examples of the "nitriles" include acetonitrile, propionitrile and the like.

Examples of the "organic acids" include acetic acid, propionic acid, trifluoroacetic acid and the like.

Compound (IX) [compound wherein $R^1$ is a hydrogen atom, nitro, halogen, phthalimido, mono(alkylcarbonyl) amino, di(alkylcarbonyl)amino or alkoxy] and Compound (XII) have the excellent GnRH antagonistic activity and the low toxicity and, therefore, can be used for preventing or treating male hormone or female hormone-dependent diseases, and can be safely used for preventing or treating diseases derived from excessive these hormones, by inhibiting gonadotropin secretion by the GnRH receptor antagonistic activity and controlling the sex hormone concentration in blood, in a mammal (for example, human being, monkey, cow, horse, dog, cat, rabbit, rat and mouse). For example, Compound (IX) and Compound (XII) are useful as an agent for preventing and (or) treating sex hormone-dependent cancers (for example, prostate cancer, uterine cancer, breast cancer, pituitary gland tumor and the like), prostatomegaly, hysteromyoma, endometriosis, precocious puberty, amenorrhea, premenstrual syndrome, multilocular ovary syndrome and pimple, as an agent for regulating reproduction in a male or a female (for example, pregnancy regulating agent, menstrual cycle regulating agent and the like), as a contraceptive for a male and a female, as an ovulation inducing agent for a female, and as an agent for treating infertility. Further, the compositions are also useful as an agent for regulating estrus of an animal in the stockbreeding field, as an agent for improving meat quality for edible meat, as an agent for promoting growth of an animal, and as an agent for promoting oviposition of fishes.

The present invention is explained in more detail by way of Examples below, but is not limited to them.

Nuclear magnetic resonance spectrum ($^1$H-NMR) is measured with Brucker DPX-300 using tetramethylsilane as an internal standard, and the whole δ value is shown in ppm. Unless indicated otherwise, % denotes % by weight, provided that, yield denotes mol/mol %.

Symbols in Examples have the following meanings.
s: singlet
d: doublet
t: triplet
m: multiplet
bs: broad singlet
J: coupling constant
Me: methyl
Et: ethyl

EXAMPLES

Reference Example 1

Preparation of 4-nitrophenylacetone t-butyl methyl ether (290 ml), ethanol (40 ml) and ethyl malonate (70.04 g, 0.437 mol) were added to magnesium ethoxide (50.00 g, 0.437 mol), which was heated to reflux for 30 minutes and returned to room temperature (hereinafter, abbreviated as Solution A). Thionyl chloride (104.04 g, 0.875 mol) was added to 4-nitrophenylacetic acid (66.00 g, 0.364 mol), which was stirred at 70–75° C. for 45 minutes. Thionyl chloride was distilled off under reduced pressure, followed by azeotropy with toluene (66 ml) two times. t-butyl methyl ether (132 ml) was added to the azeotropic residue to dissolve it, which was added dropwise to Solution A. After stirred at 65° C. for 30 minutes, the mixture was cooled to room temperature, and 2N hydrochloric acid (264 ml) was added thereto dropwise under cooling. The organic layer was separated, the aqueous layer was reverse-extracted with t-butyl methyl ether (132 ml), the organic layers were combined, and the solvent was distilled off under reduced pressure. Acetic acid (111 ml), water (74 ml) and concentrated sulfuric acid (14 ml) were added to the concentrated residue, and the mixture was refluxed at an outer temperature of 125° C. for 5 hours while stirring vigorously. After completion of the reaction, the mixture was ice-cooled, returned to room temperature, and t-butyl methyl ether (264 ml) and water (264 ml) were added thereto, followed by extraction. An aqueous saturated sodium hydrogen carbonate solution (264 ml) and ethyl acetate (80 ml) were added to the organic layer to wash the layer, followed by further washing with an aqueous saturated sodium bicarbonate solution (264 ml). After washed with brine (264 ml) twice, the solvent was distilled off under reduced pressure, and the residue was purified by silica gel column chromatography to give 4-nitrophenylacetone (48.96 g, 0.273 mol, 75%).

Reference Example 2

Preparation of 4-nitrophenylacetone

Dichloromethane (3 ml) and ethyl malonate (1.31 g, 8.15 mmol) were added to aluminium chloride (1.10 g, 8.28 mmol) (hereinafter, abbreviated as Solution B). Thionyl chloride (1.58 g, 13.25 mmol) was added to 4-nitrophenylacetic acid (1.00 g, 5.52 mol), followed by stirring at 70–75° C. for 45 minutes. Thionyl chloride was distilled off under reduced pressure, followed by azeotropy with toluene (3 ml) twice. Dichloromethane (3 ml) was added to the azeotropic residue to dissolve the residue, which was added to Solution B dropwise. After stirred for 7 hours under reflux, the reaction solution was cooled to room temperature and poured into water (10 ml). The layers were separated, and the aqueous layer was extracted with dichloromethane (3 ml). The organic layers were combined, and the solvent was distilled off under reduced pressure. After the solvent was distilled off, acetic acid (1.7 ml), water (1.1 ml) and concentrated sulfuric acid (0.21 ml) were added thereto, which was refluxed at an external temperature of 125° C. for 4 hours while stirring vigorously. After completion of the reaction, the mixture was ice-cooled, returned to room temperature, and t-butyl methyl ether (6 ml) and water (6 ml) were added thereto, followed by extraction. After the organic layer was washed with an aqueous saturated sodium hydrogen carbonate solution (6 ml) twice and brine (6 ml) twice, the solvent was distilled off under reduced pressure, and the residue was purified by silica gel column chromatography to give 4-nitrophenylacetone (0.51 g, 2.87 mmol, 52%).

Reference Example 3

Preparation of ethyl 2-amino-4-methyl-5-(4-nitrophenyl)thiophene-3-carboxylate

Ethanol (68 ml), powdery sulfur (5.83 g, 0.182 mol), ethyl cyanoacetate (20.59 g, 0.182 mol) and butylamine (13.31 g, 0.182 mol) were added to 4-nitrophenylacetone (29.61 g, 0.165 mol), and the mixture was stirred at room temperature for 2 hours. After the reaction solution was stirred for 1 hour under ice-cooling, the crystals were filtered and washed with cold ethanol (20 ml) three times. The crystals were dried under vacuum at 50° C. to give ethyl 2-amino-4-methyl-5-(4-nitrophenyl)thiophene-3-carboxylate (34.85 g, 0.114 mol, 69%).

$^1$H-NMR(300 MHz, DMSO-$d_6$) δ 1.29(t, 3H, J=7.1 Hz), 2.36(s, 3H), 4.24(q, 2H, J=7.1 Hz), 7.59(d, 2H, J=8.9 Hz), 7.67(bs, 2H), 8.23(d, 2H, J=8.9 Hz)

Reference Example 4

Preparation of ethyl 2-amino-4-methyl-5-(4-nitrophenyl)thiophene-3-carboxylate

Ethanol (4 ml), powdery sulfur (0.22 g, 6.70 mmol), ethyl cyanoacetate (0.757 g, 6.70 mmol) and butylamine (81.6 mg, 1.12 mmol) were added to 4-nitrophenylacetone (1.00 g, 5.58 mmol), and the mixture was stirred at room temperature for 15 hours. After the reaction mixture was stirred for 1 hour under ice-cooling, the crystals were filtered and washed with cold ethanol (1.5 ml) three times. The crystals were dried under vacuum at 50° C. to give ethyl 2-amino-4-methyl-5-(4-nitrophenyl)thiophene-3-carboxylate (1.36 g, 4.45 mmol, 80%).

$^1$H-NMR(300 MHz, DMSO-$d_6$) δ 1.29(t, 3H, J=7.1 Hz), 2.36(s, 3H), 4.24(q, 2H, J=7.1 Hz), 7.59(d, 2H, J=8.9 Hz), 7.67(bs, 2H), 8.23(d, 2H, J=8.9 Hz)

Reference Example 5-1

Preparation of ethyl 2-amino-5-(4-methoxyphenyl)-4-methylthiophene-3-carboxylate Ethanol (500 ml), ethyl cyanoacetate (159.4 g, 1.41 mol) and benzylamine (1.3 g, 0.012 mol) were added to 4-methoxyphenylacetone (199.3 g, 1.2 mol), and the mixture was stirred at room temperature for 6 hours. Then, powdery sulfur (38.5 g, 1.2 mol) and morpholine (52.3 g, 0.6 mol) were successively added thereto, and the mixture was stirred at 50–60° C. for 6 hours. The mixture was cooled to room temperature, ethyl acetate (2.5 l) and brine (1.5 l) were added to the reaction solution to stir and, then, the organic layer was separated. After the organic layer was dried over magnesium sulfate, the solvent was distilled off under reduced pressure to give a red brown oil (394 g). Diisopropyl ether: hexane (1:1, v/v, 400 ml) was added thereto, and the mixture was stirred at room temperature for 30 minutes, and for 1 hour under ice-cooling. The precipitated crystals were filtered, and washed with cold diisopropyl ether: hexane (1:1, v/v, 100 ml) twice. The crystals were dried under vacuum at 40° C. to give ethyl 2-amino-5-(4-methoxyphenyl)-4-methylthiophene-3-carboxylate (239.3 g, 68.4%).

$^1$H-NMR(CDCl$_3$, 300 MHz) δ 1.37(t, 3H, J=7.1 Hz), 2.28(s, 3H), 3.83(s, 3H), 4.31(q, 2H, J=7.1 Hz), 6.06(s, 2H), 6.91(d, 2H, J=8.8 Hz), 7.26(d, 2H, J=8.8 Hz)

Reference Example 5-2

Preparation of methyl 2-amino-5-(4-chlorophenyl)-4-methylthiophene-3-carboxylate The same procedures as those in Reference Example 3-1 were performed using 4-chlorophenylacetone, to give methyl 2-amino-5-(4-chlorophenyl)-4-methylthiophene-3-carboxylate.

$^1$H-NMR(CDCl$_3$, 300 MHz) δ 1.37(t, 3H, J=7.1 Hz), 2.30(s, 3H), 4.32(q, 2H, J=7.1H), 6.12(s, 2H), 7.26(d, 2H, J=8.5 Hz), 7.34(d, 2H, J=8.5 Hz)

Reference Example 5-3

Preparation of methyl 2-amino-5-(4-methoxyphenyl)-4-methylthiophene-3-carboxylate The same procedures as those in Reference Example 3-1 were performed using 4-methoxyphenylacetone, to give methyl 2-amino-5-(4-methoxyphenyl)-4-methylthiophene-3-carboxylate.

$^1$H-MR(CDCl$_3$, 300 MHz) δ 2.27(s, 3H), 3.83(s, 3H), 3.84(s, 3H), 6.05(s, 2H), 6.91(d, 2H, J=8.6 Hz), 7.26(d, 2H, J=8.6 Hz)

Reference Example 5-4

Preparation of ethyl 2-amino-4-methyl-5-phenylthiophene-3-carboxylate

The same procedures as those in Reference Example 3-1 were performed using phenylacetone, to give ethyl 2-amine-4-methyl-5-phenylthiophene-3-carboxylate.

$^1$H-NMR(CDCl$_3$, 300 MHz) δ 1.37(t, 3H, J=7.1 Hz), 2.33(s, 3H), 4.33(q, 2H, J=7.1 Hz), 6.09(s, 2H), 7.25–7.40 (m, 5H)

Reference Example 5-5

Preparation of isopropyl 2-amino-5-(4-methoxyphenyl)-4-methylthiophene-3-carboxylate The same procedures as those in Reference Example 3-1 were performed using 4-methoxyphenylacetone, to give isopropyl 2-amino-5-(4-methoxyphenyl)-4-methylthiophene-3-carboxylate.

$^1$H-NMR(CDCl$_3$, 300 MHz) δ 1.34(d, 6H, J=6.3 Hz), 2.28(s, 3H), 3.82(s, 3H), 5.21(quint, 1H, J=6.2 Hz), 6.10(s, 2H), 6.90(d, 2H, J=8.7 Hz), 7.26(d, 2H, J=8.7 Hz)

Example 1 (Corresponding to Steps 1A and 1C)

Preparation of ethyl 2-amino-4-methyl-5-(4-nitrophenyl)thiophene-3-carboxylate

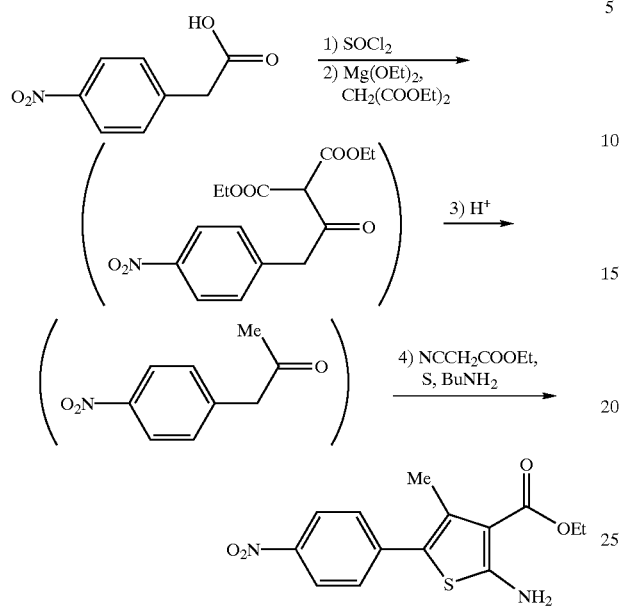

t-butyl methyl ether (880 ml), ethanol (120 ml) and ethyl malonate (212.23 g, 1.325 mol) were added to magnesium ethoxide (151.62 g, 1.325 mol), and the mixture was heated to reflux for 30 minutes and returned to room temperature (hereinafter, abbreviated as Solution C). Thionyl chloride (315.27 g, 2.650 mol) was added to 4-nitrophenylacetic acid (200.00 g, 1.104 mol), and the mixture was stirred at 70–75° C. for 45 minutes. Thionyl chloride was distilled off under reduced pressure, followed by azeotropy with toluene (200 ml) twice. t-butyl methyl ether (400 ml) was added to the azeotropic residue to dissolve the residue, which was added to Solution C dropwise. The mixture was stirred at 65° C. for 30 minutes, cooled to room temperature, and 2N hydrochloric acid (800 ml) was added thereto dropwise under ice-cooling. The organic layer was separated, the aqueous layer was reverse-extracted with t-butyl methyl ether (400 ml), the organic layers were combined and the solvent was distilled off under reduced pressure. Acetic acid (336 ml), water (224 ml) and concentrated sulfuric acid (42.4 ml) were added to the concentrated residue, and the mixture was refluxed at an external temperature of 125° C. for 5 hours while stirring vigorously. After completion of the reaction, the reaction was ice-cooled to room temperature, and t-butyl methyl ether (800 ml) and water (800 ml) were added thereto, followed by extraction. An aqueous saturated sodium hydrogen carbonate solution (800 ml) and ethyl acetate (240 ml) were added to the organic layer to wash the layer, which was further washed with an aqueous saturated sodium hydrogen carbonate solution (800 ml). After washed with brine (800 ml) twice, the solvent was distilled off under reduced pressure, followed by azeotropy with toluene (200 ml) twice. Ethyl cyanoacetate (137.33 g, 1.214 mol), ethanol (460 ml) and powdery sulfur (38.92 g, 1.214 mol) and n-butylamine (88.79 g, 1.214 mol) were added to the azeotropic residue, and the mixture was stirred at room temperature for 2 hours. The reaction mixture was stirred for 1 hour under ice-cooling, the crystals were filtered and washed with cold ethanol (400 ml). The crystals were dried under vacuum at 50° C. to give ethyl 2-amino-4-methyl-5-(4-nitrophenyl)thiophene-3-carboxylate (215.2 g, 0.702 mol, 63.6%).

$^1$H-NMR(300 MHz, DMSO-d$_6$) δ 1.29(t, 3H, J=7.1 Hz), 2.36(s, 3H), 4.24(q, 2H, J=7.1 Hz), 7.59(d, 2H, J=8.9 Hz), 7.67(bs, 2H), 8.23(d, 2H, J=8.9 Hz)

Example 2 (Corresponding to Step 2)

Preparation of ethyl 4-methyl-5-(4-nitrophenyl)-2-(3-phenylureido)thiophene-3-carboxylate

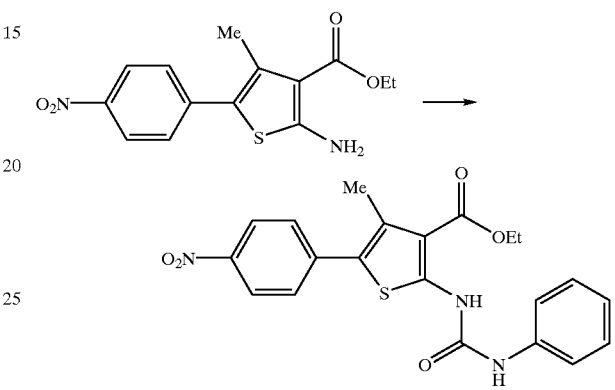

Toluene (500 ml), pyridine (12.27 g, 155.06 mmol) and phenyl isocyanate (14.58 g, 122.41 mmol) were added to ethyl 2-amino-4-methyl-5-(4-nitrophenyl)thiophene-3-carboxylate (25.00 g, 81.61 mmol), and the mixture was stirred at 95–100° C. for 4 hours. It was confirmed that starting materials were almost disappeared. After the reaction solution was stirred for 2 hours under ice-cooling, the crystals were isolated with a centrifuging machine and washed with cold toluene (150 ml). The crystals were dried under vacuum at 60° C. for 8 hours to give ethyl 4-methyl-5-(4-nitrophenyl)-2-(3-phenylureido)thiophene-3-carboxylate (32.42 g, 76.20 mmol, 93.4%)

$^1$H-NMR(300 MHz, DMSO-d$_6$) δ 1.37(t, 3H, J=7.1 Hz), 2.41(s, 3H), 4.38(q, 2H, J=7.1 Hz), 7.05(t, 1H, J=7.4 Hz), 7.33(t, 2H, J=7.9 Hz), 7.51(d, 2H, J=7.6 Hz), 7.71(d, 2H, J=8.9 Hz), 8.29(d, 2H, J=8.9 Hz), 10.36(s, 1H), 10.83(s, 1H)

Example 3 (Corresponding to Step 3)

Preparation of 1-(2,6-difluorobenzyl)-5-methyl-6-(4-nitrophenyl)-3-phenylthieno[2,3-d]pyrimidine-2,4(1H, 3H)-dione

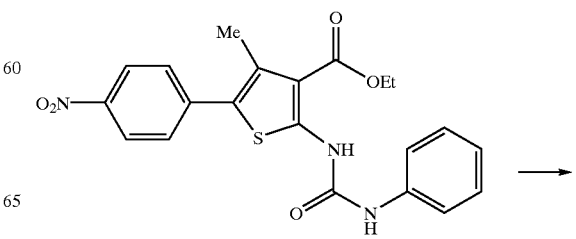

-continued

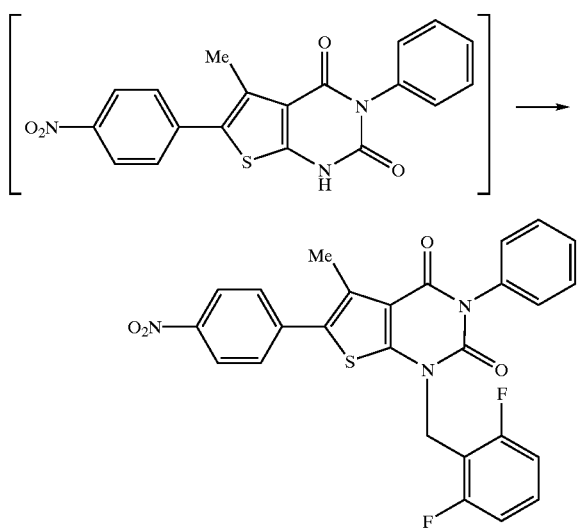

Acetonitrile (240 ml), methanol (150 ml) and 28% sodium methoxide (15.24 g, 78.97 mmol) were added to ethyl 4-methyl-5-(4-nitrophenyl)-2-(3-phenylureido)thiophene-3-carboxylate (30.00 g, 70.51 mmol), and the mixture was stirred for 1 hour while refluxing under heating. 2,6-difluorobenzyl bromide (17.52 g, 84.61 mmol) was dissolved in acetonitrile (60 ml), and the solution was added to the previous reaction mixture under refluxing. After refluxing under heating for 5 hours, 28% sodium methoxide (1.36 g, 7.05 mmol) was added thereto under reflux, and the mixture was stirred for 1 hour. The reaction mixture was cooled to room temperature, water (150 ml) was added dropwise, which was stirred at room temperature for 1 hour. The crystals were filtered and washed with water (240 ml) and diisopropyl ether/ethanol=9/1 (240 ml). The resulting crystals were suspended in ethyl acetate (600 ml), and the suspension was stirred for 1 hour under reflux. The mixture was cooled to room temperature and, after stirred for 1 hour, the crystals were filtered, washed with ethyl acetate (60 ml) and dried under vacuum at 60° C. to give 1-(2,6-difluorobenzyl)-5-methyl-6-(4-nitrophenyl)-3-phenylthieno[2,3-d]pyrimidine-2,4(1H, 3H)-dione (31.4 g, 62.12 mmol, 88.1%).

$^1$H-NMR(300 MHz, DMSO-d$_6$) δ 5.30(s, 2H), 7.05–7.55 (m, 8H), 7.74(d, 2H, J=8.8 Hz), 8.32(d, 2H, J=8.8 Hz)

Example 4 (Corresponding to Step 4)

Preparation of 5-(N-benzyl-N-methylaminomethyl)-1-(2,6-difluorobenzyl)-5-methyl-6-(4-nitrophenyl)-3-phenylthieno[2,3-d]pyrimidine-2,4(1H, 3H)-dione

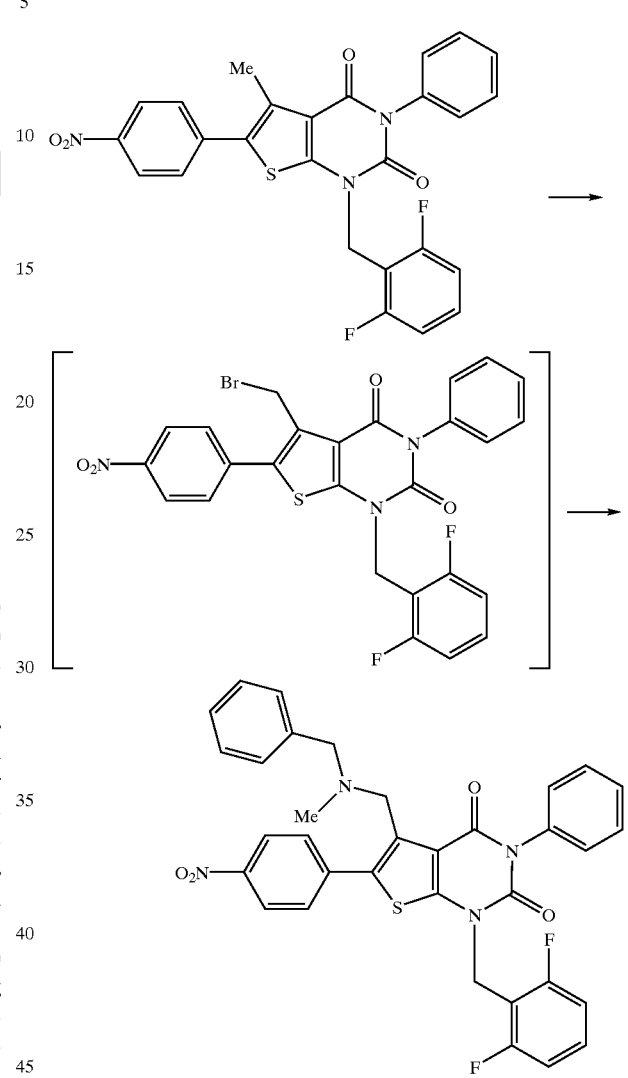

Acetonitrile (75 ml), N-bromosuccinimide (2.11 g, 11.87 mmol) and 2,2'-azobis(isobutyronitrile)(0.195 g, 1.19 mmol) were added to 1-(2,6-difluorobenzyl)-5-methyl-6-(4-nitrophenyl)-2,4(1H, 3H)-dioxo-3-phenylthieno[2,3-d]pyrimidine (5.00 g, 9.89 mmol), the mixture was heated to reflux for 20 minutes, a solution obtained by dissolving bromine (0.079 g, 0.49 mmol) in acetonitrile (3 ml) was added thereto, which was further heated to reflux for 1 hour. The reaction solution was allowed to cool to 70° C., diisopropylethylamine (1.47 g, 11.37 mmol) and N-benzylmethylamine (1.29 g, 10.38 mmol) were added successively, and the mixture was stirred for 1 hour while allowing to cool. The reaction solution was concentrated to about 25 ml, and water (10 ml) was slowly added dropwise while heating to reflux. The mixture was allowed to cool to room temperature and further stirred at 0° C. for 1 hour. The crystals were filtered, and washed with cold acetonitrile (5 ml), water (10 ml) and cold acetonitrile (5 ml) successively. The crystals were dried under vacuum at 50° C. to give 5-(N-benzyl-N-methylaminomethyl)-1-(2,6-difluorobenzyl)-5-methyl-6-(4-nitrophenyl)-3-phenylthieno[2,3-d]pyrimidine-2,4(1H, 3H)-dione (5.29 g, 8.47 mmol, 85.6%).

$^1$H-NMR(300 MHz, DMSO-d$_6$) δ 2.01(s, 3H), 3.49(s, 2H), 3.94(s, 2H), 5.30(s, 2H), 7.09–7.33(m, 9H), 7.41–7.57 (m, 4H), 8.03(d, 2H, J=8.9 Hz), 8.30(d, 2H, J=8.9 Hz)

Example 5 (Corresponding to Step 5-1)

Preparation of 6-(4-aminophenyl)-5-(N-benzyl-N-methylaminomethyl)-1-(2,6-difluorobenzyl)-3-phenylthieno[2,3-d]pyrimidine-2,4(1H, 3H)-dione

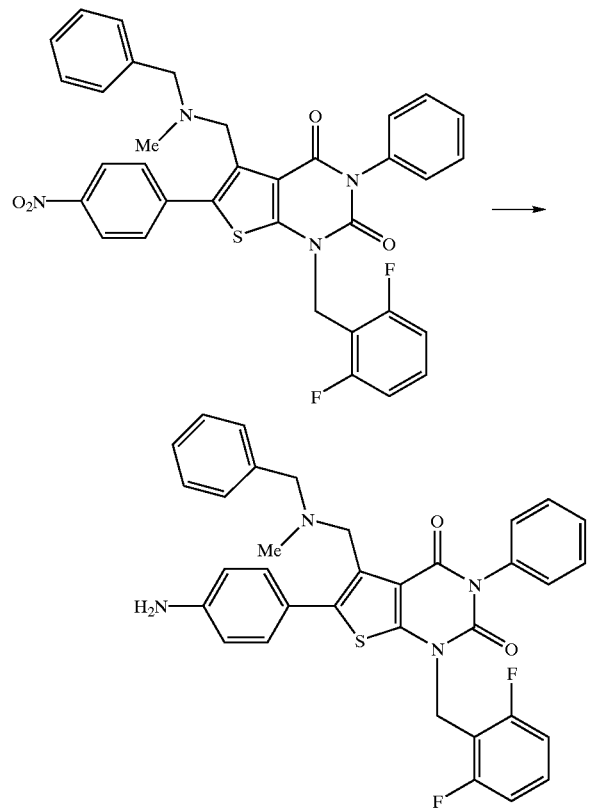

5-(N-benzyl-N-methylaminomethyl)-1-(2,6-difluorobenzyl)-5-methyl-6-(4-nitrophenyl)-3-phenylthieno[2,3-d]pyrimidine-2,4(1H, 3H)-dione (3.00 g, 4.80 mmol) was dissolved in acetic acid (6.00 ml). A 20% titanium (III) chloride solution (22.22 g, 28.82 mmol) was added thereto, and the mixture was stirred at room temperature for 1 hour (slight exothermic). Citric acid monohydrate (7.07 g) was added to the reaction solution to dissolve it, and water (30 ml) and 2-butanone (50 ml) were added thereto. 2-aminoethanol (15 ml) was added thereto while the temperature of the solution was maintained below 40° C., and the mixture was stirred at room temperature for 20 minutes. The organic layer was separated, and the aqueous layer was reverse-extracted with 2-butanone (30 ml). The organic layers were combined, which was washed by addition of an aqueous saturated sodium hydrogen carbonate solution (40 ml) and sodium chloride (7.00 g). Active carbon (0.3 g) was added to the organic layer, and the mixture was stirred at room temperature for 10 minutes. After active carbon was filtered, the organic solvent was distilled off under reduced pressure, acetonitrile (15 ml) was added thereto, and the mixture was heated to reflux for 40 minutes. The mixture was allowed to cool to room temperature for 1 hour, and water (9 ml) was slowly added dropwise. The mixture was stirred at room temperature for 30 minutes, and stirred at 0° C. for 30 minutes. The crystals were filtered and washed with cold acetonitrile/water=5/3(5 ml). The resulting crystals were dried under vacuum at 50° C. to give 6-(4-aminophenyl)-5-(N-benzyl-N-methylaminomethyl)-1-(2,6-difluorobenzyl)-3-phenylthieno[2,3-d]pyrimidine-2,4(1H, 3H)-dione (2.51 g, 4.23 mmol, 88.1%).

$^1$H-NMR(300 MHz, DMSO-d$_6$) δ 1.93(s, 3H), 3.44(s, 2H), 3.77(s, 2H), 5.27(s, 2H), 5.41(bs, 2H), 6.63(d, 2H, J=8.5 Hz), 7.09–7.56(m, 15H)

Example 6 (Corresponding to Step 5-1)

Preparation of 6-(4-aminophenyl)-5-(N-benzyl-N-methylaminomethyl)-1-(2,6-difluorobenzyl)-3-phenylthieno[2,3-d]pyrimidine-2,4(H, 3H)-dione 5-(N-benzyl-N-methylaminomethyl)-1-(2,6-difluorobenzyl)-5-methyl-6-(4-nitrophenyl)-3-phenylthieno[2,3-d]pyrimidine-2,4(1H, 3H)-dione (5.00 g, 8.00 mmol) was dissolved in acetic acid (10 ml). Iron powder (1.79 g, 32.00 mmol) was added thereto, and 5 mol/L hydrochloric acid (6.5 mmol) was slowly added thereto dropwise. After the temperature of the reaction solution became below 80° C., the reaction solution was further heated and stirred at 80° C. for 30 minutes. Citric acid monohydrate (12.00 g) was added to the reaction solution to dissolve it, water (50 ml), 2-butanone (80 ml) and 2-aminoethanol (15.0 ml) were added thereto, and the mixture was stirred at room temperature for 20 minutes. The aqueous layer was separated, and reverse-extracted with 2-butanone (50 ml). The organic layers were combined, the insolubles were filtered with Hyflo Super-Cell, and the filtrate was washed with 2-butanone (20 ml). After the aqueous layer mixed in the filtrate was removed, the mixture was washed by addition of an aqueous saturated sodium hydrogen carbonate solution (40 ml) and sodium chloride (7.00 g). The same procedures were further repeated two times. Active carbon (0.5 g) was added thereto, and the mixture was stirred at room temperature for 30 minutes. Active carbon was filtered, and the organic solvent was distilled off under reduced pressure. Acetonitrile (25 ml) was added thereto, and the mixture was heated to reflux for 40 minutes. The mixture was allowed to cool to room temperature for 1 hour, water (15 ml) was slowly added dropwise, and the mixture was stirred at room temperature for 30 minutes. After stirred at 0° C. for 30 minutes, the crystals were filtered and washed with cold acetonitrile/water=5/3 (8 ml). Drying under vacuum at 50° C. afforded crude 6-(4-aminophenyl)-5-(N-benzyl-N-methylaminomethyl-1-(2,6-difluorobenzyl)-3-phenylthieno[2,3-d]pyrimidine-2,4(1H, 3H)-dione (3.60 g, 6.05 mmol, 75.7%). Acetonitrile (18 ml) was added to the resulting crystals, which was heated to reflux for 40 minutes. The material was allowed to cool to room temperature for 1 hour, and stirred at room temperature for 1 hour. The crystals were filtered and washed with cold acetonitrile (2 ml). Drying under vacuum at 50° C. afforded 6-(4-aminophenyl)-5-(N-benzyl-N-methylaminomethyl)-1-(2,6-difluorobenzyl)-3-phenylthieno[2,3-d]pyrimidine-2,4(1H, 3H)-dione (3.10 g, 5.21 mmol, 65.2%).

Example 7 (Corresponding to Step 6-1)

Preparation of 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)-dione 6-(4-aminophenyl)-5-(N-benzyl-N-methylaminomethyl)-1-(2,6-difluorobenzyl)-3-phenylthieno[2,3-d]pyrimidine-2,4(1H, 3H)-dione (0.50 g, 0.84 mmol) was dissolved in dimethyl acetamide (2 ml), pyridine (82 μl, 1.01 mmol) was added thereto, and the mixture was stirred. Phenyl chloroformate (phenyl chlorocarbonate)(126 μl, 1.01 mmol) was added thereto dropwise under ice-cooling, and the mixture was stirred at room temperature for 2 hours. O-methylhydroxylamine hydrochloride (77.2 mg, 92.4 μmol) and triethylamine (336 μl, 2.77 mmol) were added thereto, and the mixture was stirred at 50° C. for 12 hours. Water (30 ml) was added thereto, and the mixture was vigorously stirred. The crystals were filtered, and dried under vacuum at 40° C. to give white crystals of 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)-dione (0.55 g, 98.2%).

$^1$H-NMR(300 MHz, CDCl$_3$) δ 2.03(s, 3H), 3.54(s, 2H), 3.80(s, 3H), 3.88(s, 2H), 5.35(s, 2H), 6.90(t, 2H, J=8.2 Hz), 7.12–7.36(m, 9H), 7.41–7.63(m, 6H), 6.70(d, 2H, J=8.7 Hz).

Example 8 (Corresponding to Step 6-1)

Preparation of 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)-dione O-methylhydroxylamine hydrochloride (351 mg, 4.20 mmol) was dissolved in dimethylacetamide (2 ml), pyridine (340 μl, 4.20 mmol) and phenyl chloroformate (phenyl chlorocarbonate)(527 μl, 4.20 mmol) were added thereto successively dropwise, and the mixture was stirred at room temperature for 20 minutes. 6-(4-aminophenyl)-5-(N-benzyl-N-methylaminomethyl)-1-(2,6-difluorobenzyl)-3-phenylthieno[2,3-d]pyrimidine-2,4(1H, 3H)-dione (500 mg, 0.84 μmol) and triethylamine (1.29 ml, 9.25 mmol) were added thereto, and the mixture was stirred at 50° C. for 18 hours. Water (40 ml) was added thereto, and the mixture was stirred vigorously. The crystals were filtered, and dried under vacuum at 40° C. to give white crystals of 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)-dione (0.58 g) quantitatively.

$^1$H-NMR(300 MHz, CDCl$_3$), δ 2.03(s, 3H), 3.54(s, 2H), 3.80(s, 3H), 3.88(s, 2H), 5.35(s, 2H), 6.90(t, 2H, J=8.2 Hz), 7.12–7.36(m, 9H), 7.41–7.63(m, 6H), 6.70(d, 2H, J=8.7 Hz)

Example 9 (Corresponding to Step 6-2)

Preparation of 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)dione

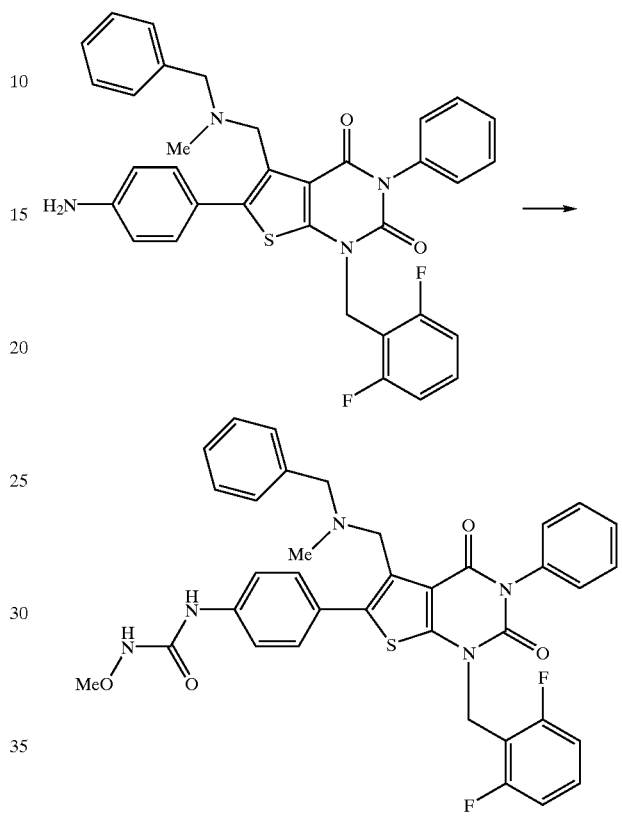

To a solution obtained by dissolving N,N'-carbonyldlimidazole (584.3 g, 3.53 mmol) in dimethylformamide (1.75 L), was added triethylamine (360.9 g, 3.57 mol) dropwise for 6 minutes under ice-cooling while maintaining below 30° C. Then, while maintaining below 30° C., a solution obtained by dissolving O-methylhydroxylamine hydrochloride (304.0 g, 3.64 mol) in dimethylformamide (1.75 L) was added dropwise thereto for 15 minutes. 6-(4-aminophenyl)-5-(N-benzyl-N-methylaminomethyl)-1-(2,6-difluorobenzyl)-3-phenylthieno[2,3-d]pyrimidine-2,4(1H, 3H)-dione (1400.0 g, 2.35 mol) was dissolved in dimethylformamide (3.5 L), which was added dropwise to the reaction mixture for 4 minutes. The mixture was stirred at 20–30° C. for 1 hour and at 50° C. for 1 hour. The mixture was cooled to 25° C., water (7.5 L) was added thereto, and the mixture was stirred at 20–30° C. for 15 hours. The crystals were filtered, and washed with water (10 L) three times. Under vacuum, the crystals were dried at 50° C. for 8 hours to give crystals of crude 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)-dione (1532.7 g). The resulting crystals were hot-dissolved in tetrahydrofuran (25 L) and filtered. The filtrate was concentrated to about 15 L under reduced pressure. The filtrate was concentrated under reduced pressure while ethanol (15 L) was continuously injected and, finally, adjusted to 15 L. The filtrate was stirred at 20–30° C. for 15 hours and 30 minutes. The crystals were filtered and washed with ethanol (2 L). The crystals were dried under vacuum at 50° C. for 23 hours to give crystals of 5-(N-benzyl-N-methylaminomethyl)-1-(2,6-difluorobenzyl)-6-[4-(3-methoxyureido)phenyl]-3-phenylthieno[2,3-d]pyrimidine-2,4(1H, 3H)-dione (1447.3 g, 2.17 mol, 92.2%).

$^1$H-NMR(300 MHz, CDCl$_3$), δ 2.03 (s, 3H), 3.54(s, 2H), 3.80(s, 3H), 3.88(s, 2H), 5.35(s, 2H), 6.90(t, 2H, J=8.2 Hz), 7.12–7.36(m, 9H), 7.41–7.63(m, 6H), 6.70(d, 2H, J=8.7 Hz)

INDUSTRIAL APPLICABILITY

According to the process of production of the present invention, thienopyrimidine derivatives having the GnRH antagonistic activity (for example, Compound (XII)) can be produced effectively and at an industrial large scale at a high yield and simple method.

What is claimed is:

1. A process for producing a compound represented by the formula(XII):

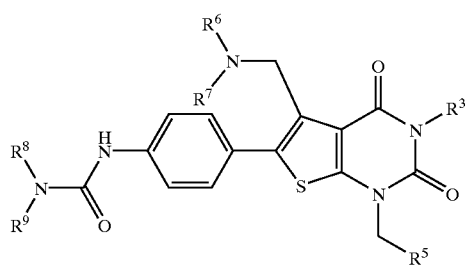

(XII)

wherein respective symbols have the same meanings as those described below, which comprises:

subjecting a compound represented by the formula(I$^a$):

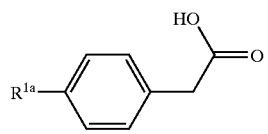

(I$^a$)

wherein R$^{1a}$ denotes nitro, phthalimido, mono(alkylcarbonyl)amino or di(alkylcarbonyl)amino, or a salt thereof, to an acid halogenating reaction, which is successively reacted with malonic acid ester and magnesium alkoxide and, thereafter, treated with an acid and, then, reacted with a sulfur and a compound represented by the formula(II):

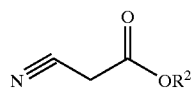

(II)

wherein R$^2$ denotes alkyl or aryl, or a salt thereof in the presence of primary amine, to obtain a compound represented by the formula (III):

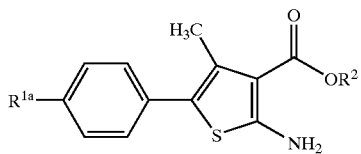

(III)

wherein respective symbols have the same meanings as those described above, or a salt thereof and, then, reacting the compound (III) or a salt thereof with a compound represented by the formula(IV):

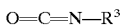

(IV)

wherein R$^3$ denotes alkyl optionally having a substituent or aryl optionally having a substituent, or a salt thereof, to obtain a compound represented by the formula (V):

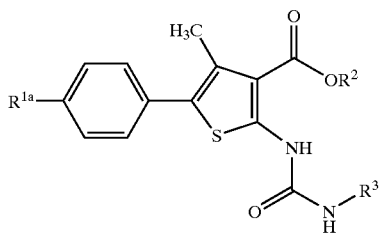

(V)

wherein respective symbols have the same meanings as those described above, or a salt thereof and, then, subjecting the compound (V) or a salt thereof to a ring closing reaction, which is reacted with a compound represented by the formula(VI):

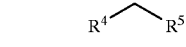

(VI)

wherein R$^4$ denotes a leaving group, and R$^5$ denotes aryl optionally having a substituent, or a salt thereof, to obtain a compound represented by the formula (VII):

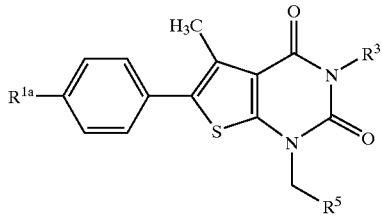

(VII)

wherein respective symbols have the same meanings as those described above, or a salt thereof and, then, subjecting the compound (VII) or a salt thereof to a brominating reaction, which is successively reacted with a compound represented by the formula (VIII):

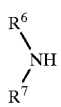

(VIII)

wherein R$^6$ and R$^7$ denote alkyl optionally having a substituent, aryl optionally having a substituent, alkoxy optionally having a substitutent, aralkyl optionally having a substituent or a heterocycle group optionally having a substituent, or a salt thereof, to obtain a compound represented by the formula (IX):

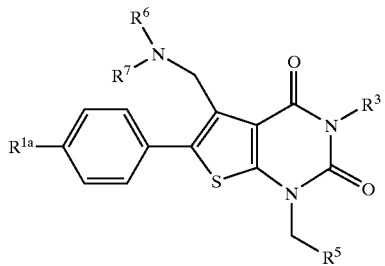
(IX)

wherein respective symbols have the same meanings as those described above, or a salt thereof, and (1) when $R^{1a}$ is nitro, subjecting the compound (IX) or a salt thereof to a reducing reaction,
(2) when $R^{1a}$ is phthalimido, subjecting the compound (IX) or a salt thereof to a deprotecting reaction, or
(3) when $R^{1a}$ is mono(alkylcarbonyl)amino or di(alkylcarbonyl)amino, subjecting the compound (IX) or a or a salt thereof to a hydrolyzing reaction, to obtain a compound represented by the formula (X):

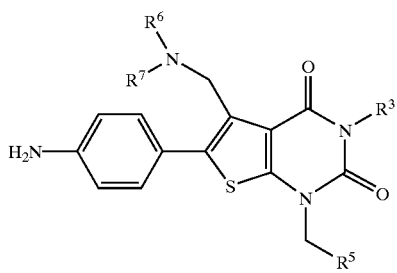
(X)

wherein respective symbols have the same meanings as those described above, or a salt thereof and, then, (i) reacting the compound (X) or a salt thereof, with halogenoformic acid ester and a compound represented by the formula (XI):

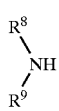
(XI)

wherein $R^8$ and $R^9$ denote a hydrogen atom, alkoxy optionally having a substituent or alkyl optionally having a substituent, or a salt thereof, or (ii) reacting the compound (X) or a salt thereof with carbonyldiimidazole and a compound represented by the formula (XI):

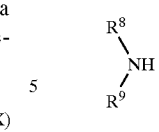
(XI)

wherein respective symbols have the same meanings as those described above or a salt thereof.

2. The process according to claim 1, wherein $R^{1a}$ is nitro.
3. The process according to claim 1, wherein $R^3$ is phenyl optionally having a substituent.
4. The process according to claim 1, wherein $R^5$ is phenyl optionally having a substituent.
5. The process according to claim 1, wherein one of $R^6$ and $R^7$ is $C_{1-3}$ alkyl, and the other of them is benzyl optionally having a substituent.
6. The process according to claim 1, wherein one of $R^8$ and $R^9$ is a hydrogen atom, and the other of them is $C_{1-3}$ alkoxy.
7. The process according to claim 1, wherein the compound (VII) or a salt thereof is subjected to a brominating reaction in the presence of bromine and a radical initiator.
8. A process for producing a compound represented by the formula(III):

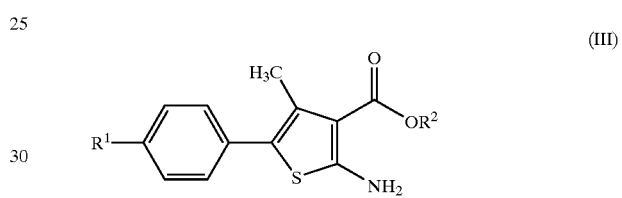
(III)

wherein respective symbols have the same meanings as those described below, or a salt thereof, which comprises: subjecting a compound represented by the formula

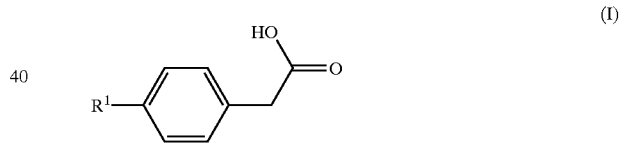
(I)

wherein $R^1$ denotes a hydrogen atom, nitro, halogen, phthalimido, mono(alkylcarbonyl)amino, di(alkylcarbonyl)amino or alkoxy, or a salt thereof, to an acid halogenating reaction, which is successively reacted with malonic acid ester and magnesium alkoxide and, thereafter, treated with an acid and, then, reacted with sulfur and a compound represented by the formula (II):

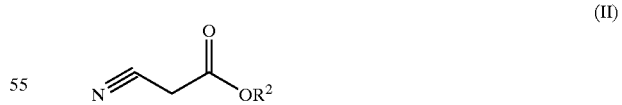
(II)

wherein $R^2$ denotes alkyl or aryl, or a salt thereof, in the presence of primary amine.

9. The process according to claim 1, wherein $R^1$ is nitro.
10. The process according to claim 1, wherein the primary amine is mono-$C_{3-8}$ alkylamine.

* * * * *